United States Patent
Bormann et al.

(10) Patent No.: US 8,825,502 B2
(45) Date of Patent: Sep. 2, 2014

(54) SYSTEM AND METHOD FOR PROVIDING PATIENT RECORD SYNCHRONIZATION IN A HEALTHCARE SETTING

(75) Inventors: Daniel S. Bormann, Waunakee, WI (US); Aaron T. Cornelius, Mount Horeb, WI (US); Timothy W. Escher, Lodi, WI (US); Sameer Grover, Sun Prairie, WI (US); Andrew M. E. Giesler, Madison, WI (US); Jason L. Hansen, Madison, WI (US); Clifford L. Michalski, Oregon, WI (US); Vassil D. Peytchev, Madison, WI (US)

(73) Assignee: Epic Systems Corporation, Madison, WI (US)

( * ) Notice: Subject to any disclaimer, the term of this patent is extended or adjusted under 35 U.S.C. 154(b) by 2676 days.

(21) Appl. No.: 10/794,933

(22) Filed: Mar. 5, 2004

(65) Prior Publication Data

US 2005/0071194 A1   Mar. 31, 2005

(51) Int. Cl.
*G06Q 50/00* (2012.01)
*G06Q 50/22* (2012.01)
*G06F 19/00* (2011.01)
*G06F 17/30* (2006.01)
*A61B 5/00* (2006.01)

(52) U.S. Cl.
CPC .......... *G06F 17/30578* (2013.01); *G06Q 50/22* (2013.01); *G06F 19/322* (2013.01); *A61B 5/0022* (2013.01)
USPC ................................................. 705/2; 705/3

(58) Field of Classification Search
CPC ... G06Q 50/22; G06Q 50/24; G06F 17/30575
USPC ......................................................... 705/2–3
See application file for complete search history.

(56) References Cited

U.S. PATENT DOCUMENTS

| | | | |
|---|---|---|---|
| 4,591,974 | A | 5/1986 | Dornbush et al. |
| 4,667,292 | A | 5/1987 | Mohlenbrock et al. |
| 4,839,806 | A | 6/1989 | Goldfischer et al. |
| 4,893,270 | A | 1/1990 | Beck et al. |
| 4,962,475 | A | 10/1990 | Hernandez et al. |
| 5,072,383 | A | 12/1991 | Brimm et al. |
| 5,072,412 | A | 12/1991 | Henderson, Jr. et al. |
| 5,072,838 | A | 12/1991 | Price, Jr. et al. |

(Continued)

FOREIGN PATENT DOCUMENTS

| WO | WO 96/27163 | 9/1996 |
|---|---|---|
| WO | WO 98/13783 | 4/1998 |

(Continued)

OTHER PUBLICATIONS

"Sunrise Knowledge-Based Orders," Advanced Clinical Solutions, ECLIPSYS, www.eclipsys.com, Dec. 2002, 4 pages.

(Continued)

*Primary Examiner* — Sind Phongsvirajati
(74) *Attorney, Agent, or Firm* — Quarles & Brady LLP

(57) ABSTRACT

A system provides an information sharing architecture that allows physically separate healthcare information systems, called "deployments," to share and exchange information. The collection of these participating deployments is referred to as the "Community," and systems within the Community sometimes store records for patients in common. The system allows participants in the Community to share information on data changes to these patients, and to reconcile concurrent and conflicting updates to the patient's record.

16 Claims, 26 Drawing Sheets

(56) References Cited

U.S. PATENT DOCUMENTS

| | | | |
|---|---|---|---|
| 5,077,666 A | 12/1991 | Brimm et al. | |
| 5,088,981 A | 2/1992 | Howson et al. | |
| 5,101,476 A | 3/1992 | Kukla | |
| 5,253,362 A | 10/1993 | Nolan et al. | |
| 5,301,105 A | 4/1994 | Cummings, Jr. | |
| 5,319,543 A | 6/1994 | Wilhelm | |
| 5,325,478 A | 6/1994 | Shelton et al. | |
| 5,361,202 A | 11/1994 | Doue | |
| 5,428,778 A | 6/1995 | Brookes | |
| 5,546,580 A | 8/1996 | Seliger et al. | |
| 5,557,515 A | 9/1996 | Abbruzzese et al. | |
| 5,574,828 A | 11/1996 | Hayward et al. | |
| 5,596,752 A | 1/1997 | Knudsen et al. | |
| 5,603,026 A | 2/1997 | Demers et al. | |
| 5,692,125 A | 11/1997 | Schloss et al. | |
| 5,724,584 A | 3/1998 | Peters et al. | |
| 5,729,735 A * | 3/1998 | Meyering | 707/10 |
| 5,748,907 A | 5/1998 | Crane | |
| 5,751,958 A | 5/1998 | Zweben et al. | |
| 5,760,704 A | 6/1998 | Barton et al. | |
| 5,772,585 A | 6/1998 | Lavin et al. | |
| 5,778,346 A | 7/1998 | Frid-Nielsen et al. | |
| 5,781,442 A | 7/1998 | Engleson et al. | |
| 5,781,890 A | 7/1998 | Nematbakhsh et al. | |
| 5,802,253 A | 9/1998 | Gross et al. | |
| 5,802,518 A * | 9/1998 | Karaev et al. | 707/9 |
| 5,823,948 A | 10/1998 | Ross, Jr. et al. | |
| 5,832,450 A | 11/1998 | Myers et al. | |
| 5,833,599 A | 11/1998 | Schrier et al. | |
| 5,838,313 A | 11/1998 | Hou et al. | |
| 5,845,253 A | 12/1998 | Rensimer et al. | |
| 5,848,393 A | 12/1998 | Goodridge et al. | |
| 5,848,395 A | 12/1998 | Edgar et al. | |
| 5,850,221 A | 12/1998 | Macrae et al. | |
| 5,867,688 A | 2/1999 | Simmon et al. | |
| 5,867,821 A | 2/1999 | Ballantyne et al. | |
| 5,899,998 A | 5/1999 | McGauley et al. | |
| 5,903,889 A | 5/1999 | de la Huerga et al. | |
| 5,915,240 A * | 6/1999 | Karpf | 705/2 |
| 5,924,074 A | 7/1999 | Evans | |
| 5,946,659 A | 8/1999 | Lancelot et al. | |
| 5,983,210 A | 11/1999 | Imasaki et al. | |
| 5,997,476 A | 12/1999 | Brown | |
| 5,999,916 A | 12/1999 | Peters et al. | |
| 6,014,631 A | 1/2000 | Teagarden et al. | |
| 6,016,477 A | 1/2000 | Ehnebuske et al. | |
| 6,021,404 A | 2/2000 | Moukheibir | |
| 6,037,940 A | 3/2000 | Schroeder et al. | |
| 6,044,381 A * | 3/2000 | Boothby et al. | 1/1 |
| 6,047,259 A | 4/2000 | Campbell et al. | |
| 6,063,026 A | 5/2000 | Schauss et al. | |
| 6,067,523 A | 5/2000 | Bair et al. | |
| 6,082,776 A | 7/2000 | Feinberg | |
| 6,139,494 A | 10/2000 | Cairnes | |
| 6,154,726 A | 11/2000 | Rensimer et al. | |
| 6,182,047 B1 | 1/2001 | Dirbas | |
| 6,188,988 B1 | 2/2001 | Barry et al. | |
| 6,263,330 B1 | 7/2001 | Bessette | |
| 6,283,761 B1 | 9/2001 | Joao | |
| 6,289,368 B1 | 9/2001 | Dentler et al. | |
| 6,304,905 B1 | 10/2001 | Clark | |
| 6,317,719 B1 | 11/2001 | Schrier et al. | |
| 6,332,167 B1 | 12/2001 | Peters et al. | |
| 6,345,260 B1 | 2/2002 | Cummings, Jr. et al. | |
| 6,401,072 B1 | 6/2002 | Haudenschild et al. | |
| 6,415,275 B1 | 7/2002 | Zahn | |
| 7,069,227 B1 * | 6/2006 | Lintel et al. | 705/4 |
| 2001/0016056 A1 | 8/2001 | Westphal et al. | |
| 2001/0016853 A1 * | 8/2001 | Kucala | 707/204 |
| 2001/0049610 A1 | 12/2001 | Hazumi | |
| 2001/0051888 A1 | 12/2001 | Mayhak, Jr. et al. | |
| 2001/0056433 A1 | 12/2001 | Adelson et al. | |
| 2002/0001375 A1 | 1/2002 | Alcott et al. | |
| 2002/0001387 A1 | 1/2002 | Dillon | |
| 2002/0002473 A1 | 1/2002 | Schrier et al. | |
| 2002/0002535 A1 | 1/2002 | Kitchen et al. | |
| 2002/0007287 A1 | 1/2002 | Straube et al. | |
| 2002/0010679 A1 * | 1/2002 | Felsher | 705/51 |
| 2003/0110059 A1 | 6/2003 | Janas, III et al. | |
| 2003/0182162 A1 * | 9/2003 | Stevens | 705/2 |
| 2003/0204420 A1 * | 10/2003 | Wilkes et al. | 705/3 |
| 2003/0220821 A1 * | 11/2003 | Walter et al. | 705/3 |
| 2004/0122709 A1 * | 6/2004 | Avinash et al. | 705/2 |

FOREIGN PATENT DOCUMENTS

| | | |
|---|---|---|
| WO | WO 99/22330 | 5/1999 |
| WO | WO 99/44162 | 9/1999 |
| WO | WO 99/63473 | 12/1999 |
| WO | WO 00/28460 | 5/2000 |
| WO | WO 00/29983 | 5/2000 |
| WO | WO 00/65522 | 11/2000 |
| WO | WO-01/98866 A2 | 12/2001 |

OTHER PUBLICATIONS

"Sunrise Clinical Manager," Advanced Clinical Solutions, ECLIPSYS, www.eclipsys.com, Dec. 2002, 4 pages.

"News & events," ECLIPSYS, www.eclipsys.com, Apr. 16, 2002, 3 pages.

"Horizon Clinicals," Mckesson Corporation, www.mckesson.com, 2003, 2 pages.

"Acute Care EMR—Solutions," Cerner Corporation, www.cerner.com, 2002-2003, 2 pages.

"Foundation," IDX Systems Corporation, www.idx.com, 1999-2004, 2 pages.

"Supporting the Work of Clinicians," IDX Systems Corporation, www.idx.com, 1999-2004, 1 page.

"Autonomy Update™," production brief, 2 pages.

"Brio.Portal," product information sheet, 1 page.

"Portal-in-a-Box™," Product Brief, Autonomy Inc., www.automony.com, Apr. 2002, 6 pages.

"Actuate Software," Sun Solutions Catalog, Actuate Corporation & Sun Microsystems, www.sun.com, 2002, 24 pages.

Hazumi et al., "Development of Electronic Medical Record System," NEC Research & Development, vol. 41, No. 1, Jan. 2000, pp. 102-105.

McDonald et al., "The Regenstrief Medical Record System: A quarter century experience," International Journal of Medical Informatics, vol. 54, 1999, pp. 225-253.

"CDR-Web," Reliance Software Systems, Website, 2000, 1 page.

Marietti, "O'Pioneers!," Healthcare Informatics, Website, May 1999, 9 pages.

Johnson, "Today's CDRs: The Elusive Complete Solution,"Healthcare Informatics, (Website), Jul. 1997, 7 pages.

Andrew et al., "Computer-Based Patient Records—Venturing Off the Beaten Path: It's Time to Blaze New CPR Trails," Healthcare Informatics, (Website), May 1997, 17 pages.

"EMR Features," Care Is #1, 1999-2000, 1 page.

"Enterprise Systems Management," Cerner Corporation, www.cerner.com, Sep. 13, 2001, 5 pages.

"HealthMatics™ Office", Healthmatics Office, Website, 3 pages, (date unknown).

CliniComp, Intl., Website, 1999-2000, 1 page.

"ExcelCare Windows", Website, 2 pages (date unknown).

"IC-Chart Information", Integreat, Website, 1 page, (date unknown).

"Managing mail messages with rules," Microsoft Outlook Help Manual, Website, Version 6, 5 pages Jun. 24, 2002.

Mercando, "Appointment Scheduling on Computer", PACE, vol. 20, Jul. 1997, pp. 1860-1862.

EncounterPRO, the Workflow Enabled CPR/EMR from JMJ Technologies, JMJ Technologies, Inc., www.jmjtech.com, Nov. 8, 2002, 6 pages.

"Expeditor Systems—The Patient Flow Systems Experts", Expeditor Systems, www.expeditor.com, 2001, 3 pages.

"Working with Patient Lists," EpicCare Inpatient Electronic Medical Record Jul. 2000 User's Guide, Epic Systems Corp., Section 10.5-10.6, 3 pages.

(56) References Cited

OTHER PUBLICATIONS

"Patient Lists," EpicCare Inpatient Electronic Medical Record Jul. 2000 User's Guide, Epic Systems Corp., Section 11.3-11.4, 3 pages.
"Oacis—Census Management," DINMAR (U.S.) Inc., www.oacis. com, 2002, 2 pages.
Grimson et al., "Interoperability issues in Sharing Electronic Healthcare Records—the Synapses Approach," IEEE, 1997, pp. 180-185.
"Clinician Documentation with EMR,"CliniComp; INTL., www. clinicomp.com, 1999-2002, 1 page.
"Essentris™ CPOE", CliniComp, INTL., www.clinicomp.com, 1999-2002, 2 pages.
"Essentris™ GDR,"CliniComp, INTL., www.clinicomp.com, 1999-2002, 2 pages.
"Intensivist Tools," CliniComp, INTL., www.clinicomp.com, 1999-2002, 2 pages.
"CMRxp—Computerized Medical Records Powered by Experience!!," Electronic Medical Records (EMR)xp Experience, ChartCare, Inc., www.chartcare.com, Mar. 5, 2003, 2 pages.
"Dr-InBasket-Lab Results, Messaging and To-Do's," ChartCare, Inc., www.chartcare.com, Mar. 5, 2003, 3 pages.
"PatInfo—Patient Information Handouts," PatInfo—Patient Demographics Software, ChartCare, Inc., www.chartcare.com, Mar. 5, 2003, 2 pages.
"Recall-Patient Health Maintenance," ChartCare, Inc., www. chartcare.com, Mar. 5, 2003, 3 pages.
"LabTrack—Lab Ordering & Results Tracking," LabTrack—Lab Result Tracking Software, ChartCare, Inc., www.chartcare.com, Mar. 5, 2003, 3 pages.
"Rx-MedTrack—Prescription Writing/Medication Tracking," Rx-MedTrack—Prescription Writing Software, ChartCare, Inc., www.chartcare.com, Mar. 5, 2003, 2 pages.
"The Right Tools," Product Description, Integreat Inc., www.igreat. com, 2003, 1 page.
"IC-Chart Additional Modules," Integreat Inc., www.igreat.com, 2003, 2 pages.
"Services," Integreat Inc., www.igreat.com, 2003, 2 pages.
"Synapses-at a Glace," The Synapses Public Website, www.cs.tcd. ie/synapses/public.html, 2 pages, (date unknown).
M.J. Wilson, "Synapses, for partners at TEHR-E 97," www.cs.tcd.ie/ synapses/public.html, Oct. 31, 1997, 4 pages.
Grimson et al., "Federated Healthcare Record Server—the Synapses paradigm,"Synapses—Medical Informatics—Public Website—Technical Description, www.cs.tcd.ie/synapses/public.html, 32 pages, (date unknown).
"Federated Healthcare Records Server," www.cs.tcd.ie/synapses/ public.html, 5 pages, (date unknown).
Berry et al., Client Interfaces to Synapses Record Server Using COBRA, Presentation, 85 pages, (date unknown).
Grimson et al., "Federated Healthcare Records—ODP Specification of Synapses—version 2," Part 1, Introduction, Trinity College Dublin, Health Telematics Programme, Synapses HC 1045, 1999, 13 pages.
Barber et al., "Federated Healthcare Records Server—ODP Specification of Synapses—version 2," Part 2, Enterprise ViewPoint, Trinity College Dublin, Health Telematics Programme, Synapses HC 1046, 1999, 84 pages.
Grimson et al., "Federated Healthcare Records Server—ODP Specification of Synapses—version 2," Part 3, Information Viewpoint, Trinity College Dublin, Health Telematics Programme, Synapses HC 1046, 1999, 67 pages.
Berry et al., "Federated Healthcare Records Server—ODP Specification of Synapses—version 2," Part 4, Computation Viewpoint, Trinity College Dublin, Health Telematics Programme, Synapses HC 1046, 1999, 106 pages.
Berry et al., "Federated Healthcare Records Server—ODP Specification of Synapses—version 2," Part 5, Engineering/Technology Viewpoint, Trinity College Dublin, Health Telematics Programme, Synapses HC 1046, 1999, 32 pages.
O'Moore et al., "Federated Healthcare Records Server—ODP Specification of Synapses—version 2," Part 6, Introduction, Trinity College Dublin, Health Telematics Programme, Synapses HC 1046, 1999, 56 pages.
"Federated Healthcare Records Server—ODP Specification of Synapses—version 2," Annex 1, Glossary of Terms, Trinity College Dublin, Health Telematics Programme, Synapses HC 1046, 1999, 11 pages.
"Federated Healthcare Records Server—ODP Specification of Synapses—version 2," Annex 3, Synapses Contact names and addresses, Trinity College Dublin, Health Telematics Programme, Synapses HC 1046, 1999, 4 pages.
Kalra et al., "The SynEx Project," www.phcsg.or.uk.com, 12 pages, (date unknown).
Jung et al., "Synapses/SynEx goes XML," Dept. of Computer Science, Trinity College Dublin, 6 pages, (date unknown).
Wang et al., "A COBRA-Based Object Framework with Patient Identification Translation and Dynamic Linking—Methods for Exchanging Patient Data," Methods of Information in Medicine, vol. 38, 1999, pp. 56-65.
"Ping—The Personal Internetworked Notary and Guardian," Clinical and Public Health Informatics—Children's Hospital Information Program, http://www.chip.org/research/ping.htm, Sep. 11, 2001, 18 pages.
Lamehamedi et al., "Data Replication Strategies in Grid Environments," Fifth International Conference on Algorithms and Architectures for Parallel Processing, Oct. 23-25, 2002, 6 pages.
Collins-Sussman et al., "Copying Changes Between Branches", Version Control with Subversion, Sebastopol, CA: O'Reilly Media, 1st Ed., Chapter 4: Branching and Merging, 2002, 8 pages.
Gray et al., "Scaleable Replicated Databases," http://research. microsoft.com/~gray/talks, Mar. 4, 1998, 25 pages.
Gray et al., "The Dangers of Replication and a Solution," Proc. ACM SIGMOD Conference, May 1996, pp. 173-182.

* cited by examiner

FIG. 11

| Patient Database Record 115781; Demographics Update History Table ||
|---|---|
| Current Generation: 5 ||
| Deployment | Generation |
| A | 1 |
| B | 5 |
| C | 4 |
| D | 3 |
| E | 2 |

| Current Generation ||
|---|---|
| Deployment | Generation |
| A | 1 |

| Current Generation ||
|---|---|
| Deployment | Generation |
| B | 2 |

| Update History Table ||
|---|---|
| Deployment | Generation |
| A | 1 |

| Current Generation ||
|---|---|
| Deployment | Generation |
| C | 3 |

| Update History Table ||
|---|---|
| Deployment | Generation |
| A | 1 |
| B | 2 |

| Current Generation ||
|---|---|
| Deployment | Generation |
| B | 2 |

562 ↓

| Current Generation ||
|---|---|
| Deployment | Generation |
| B | 2 |

| Current Generation ||
|---|---|
| Deployment | Generation |
| B | 2 |

| Update History Table ||
|---|---|
| Deployment | Generation |
| A | 1 |

572

574 ↓

| Current Generation ||
|---|---|
| Deployment | Generation |
| C | 3 |

| Update History Table ||
|---|---|
| Deployment | Generation |
| A | 1 |
| B | 2 |

| Current Generation | |
|---|---|
| Deployment | Generation |
| C | 3 |

| Update History Table | |
|---|---|
| Deployment | Generation |
| A | 1 |
| B | 2 |

| Current Generation | |
|---|---|
| Deployment | Generation |
| A | 5 |

| Update History Table | |
|---|---|
| Deployment | Generation |
| A | 1 |
| B | 2 |
| C | 4 |

588

SYSTEM AND METHOD FOR PROVIDING PATIENT RECORD SYNCHRONIZATION IN A HEALTHCARE SETTING

CROSS-REFERENCE TO RELATED APPLICATIONS

This application claims benefit of the following United States Provisional Applications: Ser. No. 60/507,419, entitled "System And Method For Providing Patient Record Synchronization In A Healthcare Setting" filed Sep. 30, 2003, Ser. No. 60/519,389, entitled "System And Method Of Synchronizing Data Sets Across Distributed Systems" filed Nov. 12, 2003, Ser. No. 60/533,316, entitled "System And Method Of Synchronizing Category Lists And Master Files Across Distributed Systems" filed Dec. 30, 2003, the disclosures of which are hereby expressly incorporated herein by reference.

TECHNICAL FIELD

This patent relates generally to health record management, and more particularly, this patent relates to a system and method for providing an information sharing architecture that allows physically separate health care information systems to share and exchange information.

BACKGROUND

Many healthcare professionals and most healthcare organizations are familiar with using information technology and accessing systems for their own medical specialty, practice, hospital department, or administration. While these systems servicing these entities have proven that they can be efficient and effective, they have largely been isolated systems that have managed electronic patient data in a closed environment. These systems collected, stored, and viewed the data in homogenous and compatible IT systems often provided by a single company. Minimal, if any, connections to the outside world or "community" were established which eased the protection of patient data immensely. Current interfaces commonly used to communicate between systems have inherent limitations.

Increased computerization throughout the healthcare industry has given rise to a proliferation of independent systems storing electronic patient data. However, at the point of delivery, more care is being moved into the community and shared among different professionals and organizations. These changes require that patients' records must be transferred and combined. Many of the existing systems are capable of accessing data from others in their own hospital, hospital group, healthcare district, or organization. However, these islands of information are typically not capable of linkage and sharing of information with other islands in the community. Furthermore, as more systems are interconnected, the linkages and sharing problems increase exponentially and become unmanageable.

BRIEF DESCRIPTION OF THE DRAWINGS

FIG. 11 is an exemplary block diagram illustrating an update history table for a demographics group of a patient record.

FIGS. 19A-L illustrates exemplary current generations and update history tables for a number of deployments.

DETAILED DESCRIPTION

Figure 1:
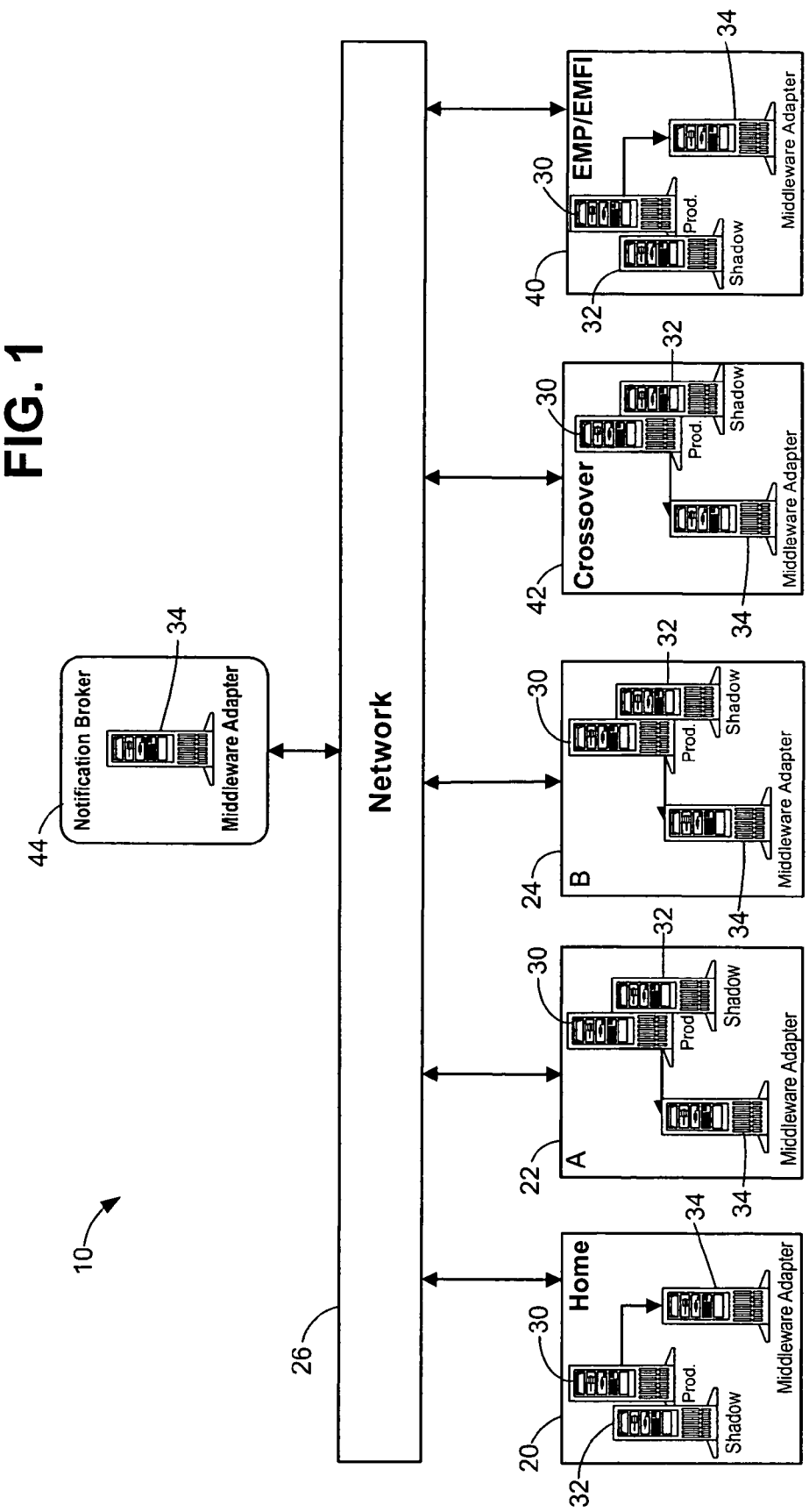
FIG. 1 is an embodiment of an exemplary system to provide an information sharing architecture that allows physically separate health care information systems to share and exchange information.

FIG. 1 illustrates an embodiment of an exemplary system 10 to provide an information sharing architecture that allows physically separate healthcare information systems, called "deployments," to share and exchange information. The collection of these participating deployments is referred to as the "Community," and systems within the Community sometimes store records for patients in common. The system 10 allows participants in the Community to share information on data changes to these patients, and to reconcile concurrent and conflicting updates to the patient's record.

The system 10 of FIG. 1 shows three deployments 20-24, labeled Home, A, and B. Home deployment 20 is operatively coupled to deployments A 22 and B 24 via the network 26.

The deployments 20-24 may be located, by way of example rather than limitation, in separate geographic locations from each other, in different areas of the same city, or in different states. Although the system 10 is shown to include the deployment 20 and two deployments A 22 and B 24, it should be understood that large numbers of deployments may be utilized. For example, the system 10 may include a network 26 having a plurality of network computers and dozens of deployments 20-24, all of which may be interconnected via the network 26.

Each record that is exchanged throughout the system may be managed, or "owned," by a specific deployment. The deployment owning a record is referred to as the record's "home deployment." When a record is accessed for the first time from a deployment other than its home deployment, referred to as a "remote deployment," the home deployment may send a copy of the record to the requesting remote deployment. The remote deployment may send its updates to the home deployment. The home deployment may coordinate the updates it receives from remote deployments by checking for conflicting data, before publishing the consolidated updates back to the Community of deployments. While the home deployment may have greater responsibility for the records it stores and manages there, it has no greater role in the general system than do the other deployments.

By convention, examples throughout this patent involve records homed on the deployment 20 labeled Home. It is important to note that the use of Home as the basis for examples would seem to suggest an inherently greater role for the home deployment 20. In fact, all three deployments 20-24 are peers, and each act as home to a subset of the system 10's records. In other words, "home" is merely an arbitrary convention for discussion.

At any given time, the home deployment for a given patient record may need to be changed because the patient moved or for some other infrastructural reason. A utility may be provided to allow authorized users at the home deployment to search for a patient record homed there and initiate a re-home process for the patient record.

The network 26 may be provided using a wide variety of techniques well known to those skilled in the art for the transfer of electronic data. For example, the network 26 may comprise dedicated access lines, plain ordinary telephone lines, satellite links, local area networks, wide area networks, frame relay, cable broadband connections, synchronous optical networks, combinations of these, etc. Additionally, the network 26 may include a plurality of network computers or server computers (not shown), each of which may be operatively interconnected in a known manner. Where the network 26 comprises the Internet, data communication may take place over the network 26 via an Internet communication protocol.

The deployments 20-24 may include a production server 30, a shadow server 32, and a dedicated middleware adaptor 34. The production server 30 and shadow server 32 may be servers of the type commonly employed in data storage and networking solutions. The servers 30 and 32 may be used to accumulate, analyze, and download data relating to a healthcare facility's medical records. For example, the servers 30 and 32 may periodically receive data from each of the deployments 20-24 indicative of information pertaining to a patient.

The production servers 30 may be referred to as a production data repository, or as an instance of a data repository. Due to the flexibility in state-of-the-art hardware configurations, the instance may not necessarily correspond to a single piece of hardware (i.e., a single server machine), although that is typically the case. Regardless of the number and variety of user interface options (desktop client, Web, etc.) that are in use, the instance is defined by the data repository. Enterprise reporting may be provided by extracting data from the production server 30, and forwarding the data to reporting repositories. Accordingly, although often configured in a one-to-one correspondence with the production server 30, the reporting repository may be separate from the production server 30.

The shadow servers 32 are servers optionally dedicated as near-real time backup of the production servers 30, and are often used to provide a failover in the event that a production server 30 becomes unavailable. Shadow servers 32 are used to improve system performance for larger systems as they provide the ability to offload display-only activity from the production servers 30.

The deployments 20-24 may also include a middleware adapter machine 34 which provides transport, message routing, queuing and delivery/processing across a network for communication between the deployments 20-24. To allow for scaling, there may be several middleware adapters 34 that together serve a deployment. For purposes of this discussion, however, all machines that form a "pairing" (production server 30 and one or more middleware adapters) will be collectively referred to as a deployment. The presence of the middleware adapters 34 is not essential to this discussion and they are shown only as a reminder that messaging is necessary and present, and for uniformity with examples/diagrams.

As the patient is the center of each healthcare experience, the information to be exchanged revolves around the patient and grows into a number of areas that, while related (they apply to the patient), serve different and distinct purposes. This includes, for example, the exchange of clinical information. However, the system provides techniques and conventions for the exchange of non-clinical information as well, including information outside the healthcare domain altogether. As used herein, the term "record" generally refers to a collection of information that might extend beyond the clinical information some might typically expect to make up a medical chart, per se.

The two types of records that most require ID tracking/management are patient records (a single file for each patient), and master file records. In this document "master file" denotes a database (a collection of data records) which is relatively static in nature, and which is primarily used for reference purposes from other more dynamic databases. For example, a patient database is relatively dynamic, growing and changing on a minute-by-minute basis; dynamic databases are comprised of records that are created as part of the workflow of software applications, such as orders and medical claims. On the other hand, a reference list of all recognized medical procedure codes, or of all recognized medical diagnoses, is relatively more static and is used for lookup purposes, and so would be referred to as a master file.

The patient record IDs (identification numbers) and the related record IDs may be coordinated across the Community by a dedicated central server that does not host healthcare application workflows, the Enterprise Master Patient Index (EMPI)/Enterprise Master File Index (EMFI) agent 40. The EMPI is the agent used to coordinate patient record IDs across the system 10, and the EMFI is the agent used to coordinate master file IDs across the system 10. This server may also function as the coordinator managing (minimizing) patient duplicate records across deployments. The EMPI/EMFI deployment 40 is aware of the home deployment for all the patients in the Community.

Each deployment 20, 22, 24, may maintain its own static and dynamic records. For example, the same specific medical order may have one local identification number (ID) at one deployment, and a different local ID at another deployment. Such deployments must agree to use a data mapping technique to resolve foreign keys contained within a patient record that arrives from another deployment. This data mapping process is described in more detail in the section titled Data Mapping.

The EMPI/EMFI server 40 is likely a separate machine running a scaled-down repository. As shown in FIG. 1, it is backed by a shadow server 32, and paired with middleware adapter 34.

A patient record is comprised of one or more "events."

An event is a data structure which stores all information relevant to a specific situation (typically though not necessarily clinical) that occurs at a specific time. Examples of events include a visit to a doctor's office, or an event that initially registers the patient with the healthcare organization. An event is composed of "data elements."

Data elements (sometimes referred to as "fields" or "columns") are a specific type of information related to the record. Examples of data elements include the patient's blood pressure, the cost of a procedure, or a doctor's phone number.

"Store-Once" data elements are shared across all events in a patient's record. Examples include the patient's birth date and eye color. These data elements either do not change over time, or if they do it is not necessary to associate the changes with specific events in the patient's record.

"Event Data" is associated with a specific event. Examples include the patient's blood pressure and symptoms for a specific visit. This information is not typically meaningful outside the event.

For effective patient synchronization, it is necessary that every deployment be aware of the other participating deployments in the Community. Numerous settings are provided in the community global settings to make a deployment "community aware."

Administrators are able to assign community-wide unique identifiers to each deployment. This is important to uniquely identify a deployment when processing incoming and outgoing messages for patient synchronization. These settings are used to notify all the deployments of the software version of each deployment in the Community. This helps to effectively step up or step down version-dependent data in the synchronization messages.

Any changes to a deployment's software version are published to the Community, so that each deployment is aware of the change. Administrators are able to activate and deactivate deployments in a Community. This way, a deployment can start or stop participating in the Community at any time.

Those persons of ordinary skill in the art will appreciate that every event in a patient record has information stored in it to easily determine the deployment that owns the event. This may be the deployment that created the event in the patient record.

The crossover server 42 allows deployments to operate at differing release versions of system software. The crossover server 42 provides storage/management for records that are extended beyond the data model available at their home deployments. The crossover server 42 allows a good deal of autonomy at the deployment level in that it provides the latitude for deployments to upgrade their version of system software on different timelines. This creates a situation where a record is homed on a deployment that, due to updates by another deployment, can no longer accommodate all of the data elements in the record. For example, if remote deployment R is at version 2007 and updates a patient record, and the patient's record is homed at deployment H which is on version 2006, deployment R may have collected new data elements that were introduced in version 2007, and so which cannot be stored in H's version 2006-based system. In this case, the model will request assistance from the crossover server—a deployment that meets or exceeds the version of any other deployment in the system 10. When the crossover server 42 is used, the record's logical home deployment will remain the same, but the physical home for the patient record will move to the crossover server 42. Like the EMPI/EMFI agent 40, the crossover server 42 is a deployment, albeit a special deployment that does not own patient and other dynamic records, and does not host workflow. The crossover server 42 is backed by a shadow server 32, and paired with middleware adapter service 34. The crossover server 42 is described in more detail in the Version Skew section below.

Remote deployments may be "subscribed" to records when they request (pull) a copy of a record from the record's home deployment. Remote deployments may send all changes they make to the patient record to the home deployment via the middleware adapter. In this manner, the design of system 10 ensures that a patient's home deployment always has the latest information about the patient's record. The home deployment publishes the updates it receives from remote deployments back into the Community.

Through the subscription process, the remote deployment may automatically be signed up to receive updates to the patient record or portion of the patient record as they occur at other deployments. When the home deployment receives updates from a remote deployment and knows that other deployments are subscribed to the record, the updates may be published to a dedicated "notification broker" server 44. The notification broker 44 may then send the updates to all subscribed deployments, via the middleware adapter 34. The notification broker 44 is a publication/subscription manager that is responsible for, as requested by participants in the system 10, registering/unregistering subscribers and distributing messages (typically containing record updates) to active subscribers. The notification broker 44 is not a typical deployment in that its repository primarily includes a list of active subscribers, the topics they are subscribed to, and other technical details about messaging.

Figure 2:
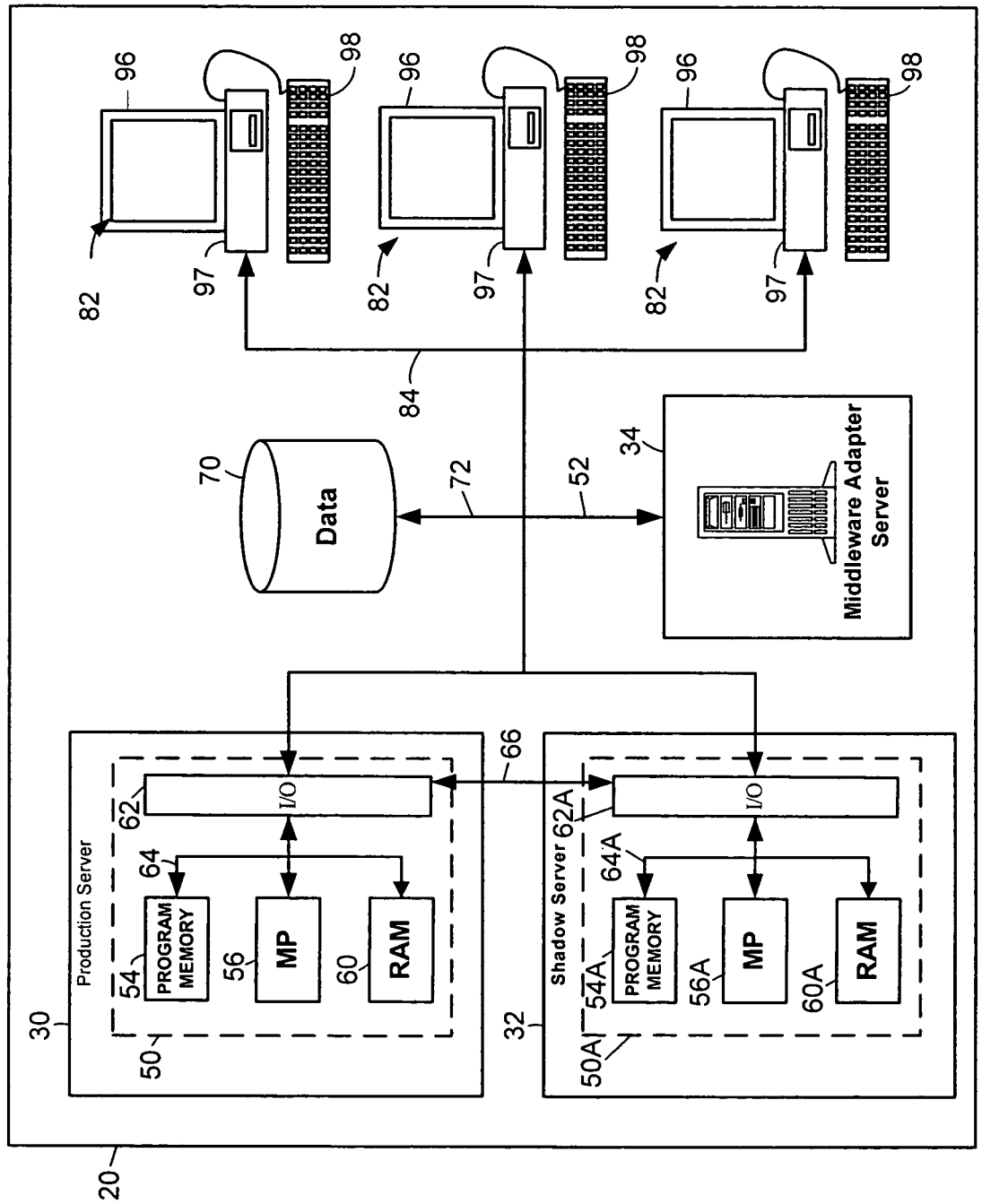
FIG. 2 is an exemplary schematic diagram of several system components located in a deployment.

FIG. 2 is a schematic diagram 20 of one possible embodiment of several components located in deployment 20 labeled Home from FIG. 1. One or more of the deployments 20-24 from FIG. 1 may have the same components. Although the following description addresses the design of the healthcare facilities 20, it should be understood that the design of one or more of the deployments 20-24 may be different than the design of other deployments 20-24. Also, deployments 20-24 may have various different structures and methods of operation. It should also be understood that the embodiment shown in FIG. 2 illustrates some of the components and data connections present in a deployment, however it does not illustrate all of the data connections present in a typical deployment. For exemplary purposes, one design of a deployment is described below, but it should be understood that numerous other designs may be utilized.

One possible embodiment of one of the production servers 30 and one of the shadow servers 32 shown in FIG. 1 is included. The production server 30 may have a controller 50 that is operatively connected to the middleware adapter 34 via a link 52. The controller 50 may include a program memory 54, a microcontroller or a microprocessor (MP) 56, a random-access memory (RAM) 60, and an input/output (I/O) circuit 62, all of which may be interconnected via an address/data bus 64. It should be appreciated that although only one microprocessor 56 is shown, the controller 50 may include multiple microprocessors 56. Similarly, the memory of the controller 50 may include multiple RAMs 60 and multiple program memories 54. Although the I/O circuit 62 is shown as a single block, it should be appreciated that the I/O circuit 62 may include a number of different types of I/O circuits. The RAM (s) 60 and program memories 54 may be implemented as semiconductor memories, magnetically readable memories, and/or optically readable memories, for example. The controller 50 may also be operatively connected to the shadow server 32 via a link 66. The shadow server 50A, if present in the deployment 20, may have similar components, 50A, 54A, 56A, 60A, 62A, and 64A.

All of these memories or data repositories may be referred to as machine-accessible mediums. For the purpose of this description, a machine-accessible medium includes any mechanism that provides (i.e., stores and/or transmits) information in a form accessible by a machine (e.g., a computer, network device, personal digital assistant, manufacturing tool, any device with a set of one or more processors). For example, a machine-accessible medium includes recordable/non-recordable media (e.g., read only memory (ROM); random access memory (RAM); magnetic disk storage media; optical storage media; flash memory devices), as well as electrical, optical, acoustical or other form of propagated signals (e.g., carrier waves, infrared signals, digital signals); etc.

The deployments 20-24 may have a data repository 70 via a link 72, and a plurality of client device terminals 82 via a network 84. The links 52, 66, 72 and 84 may be part of a wide area network (WAN), a local area network (LAN), or any other type of network readily known to those persons skilled in the art.

The client device terminals 82 may include a display 96, a controller 97, a keyboard 98 as well as a variety of other input/output devices (not shown) such as a printer, mouse, touch screen, track pad, track ball, isopoint, voice recognition system, etc. Each client device terminal 82 may be signed onto and occupied by a healthcare employee to assist them in performing their duties.

Typically, the servers 30, 32 store a plurality of files, programs, and other data for use by the client device terminals 82 and other servers located in other deployments. One server 30, 32 may handle requests for data from a large number of client device terminals 82. Accordingly, each server 30, 32 may typically comprise a high end computer with a large storage capacity, one or more fast microprocessors, and one or more high speed network connections. Conversely, relative to a typical server 30, 32, each client device terminal 82 may typically include less storage capacity, a single microprocessor, and a single network connection.

Overall Operation of the System

One manner in which an exemplary system may operate is described below in connection with a block diagram overview and a number of flow charts which represent a number of routines of one or more computer programs.

As those of ordinary skill in the art will appreciate, the majority of the software utilized to implement the system 10 is stored in one or more of the memories in the controllers 50 and 50A, or any of the other machines in the system 10, and may be written at any high level language such as C, C++, C#, Java, or the like, or any low-level, assembly or machine language. By storing the computer program portions therein, various portions of the memories are physically and/or structurally configured in accordance with the computer program instructions. Parts of the software, however, may be stored and run locally on the workstations 82. As the precise location where the steps are executed can be varied without departing from the scope of the invention, the following figures do not address which machine is performing which functions.

Figure 3:
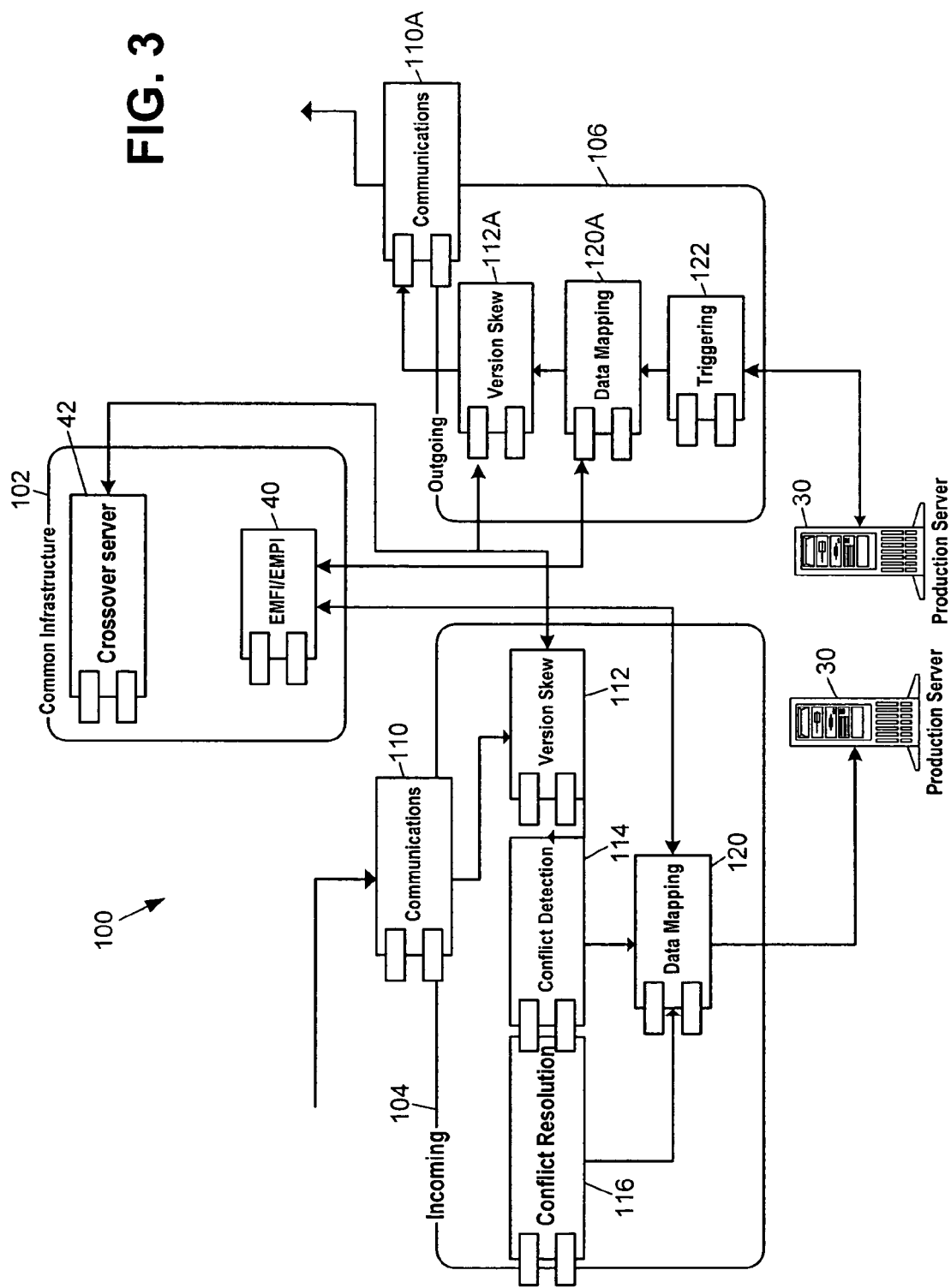
FIG. 3 is an exemplary block diagram overview of several functional components in a deployment within the system.

FIG. 3 is an exemplary block diagram overview 100 of several functional components in a deployment within the system 10. The overview 100 includes one or more production servers 30 that are used to store and maintain an electronic patient record, possibly employing a database management system as the data store. The production servers 30 may provide high-availability and data redundancy through failover and shadow servers in order to ensure uninterruptible access to the patient record.

The collection of components illustrated in overview 100 also includes a group of common infrastructure components 102, a group of incoming processing components 104 and a group of outgoing processing components 106. The group of common infrastructure components 102 includes the crossover server 42 and the EMFI/EMPI server 40. As previously mentioned, the EMFI/EMPI server 40 can provide a mechanism for coordinating master files across deployments as well as providing a way to coordinate person identities across deployments.

The group of incoming processing components 104 includes a communication agent 110 to provide reliable transport for synchronizing a patient record and a version skew agent 112 which is used to identify and handle the need to distribute record changes to multiple versions of system software. The group of incoming processing components 104 may also include a conflict detection agent 114, a conflict resolution agent 116, and a data mapping agent 120. The conflict detection agent 114 provides automated detection of cases where the changes in one deployment may be in conflict with changes made in another deployment. The conflict resolution agent 116 provides automated resolution of certain cases where conflict was detected, and for the cases which require user intervention, provides the necessary tools for the user actions. The data mapping agent 120 converts deployment specific data values from a normalized form when needed. EMPI and EMFI 40 communicate the normalized form to the data mapping agent 120 at the deployments.

The group of outgoing processing components 106 may include a triggering agent 122, a data mapping agent 120A, a version skew agent 112A and a communication agent 110A. The triggering agent 122 is the sub-system which detects changes and user actions, which need to be communicated to the Community.

Figure 4:
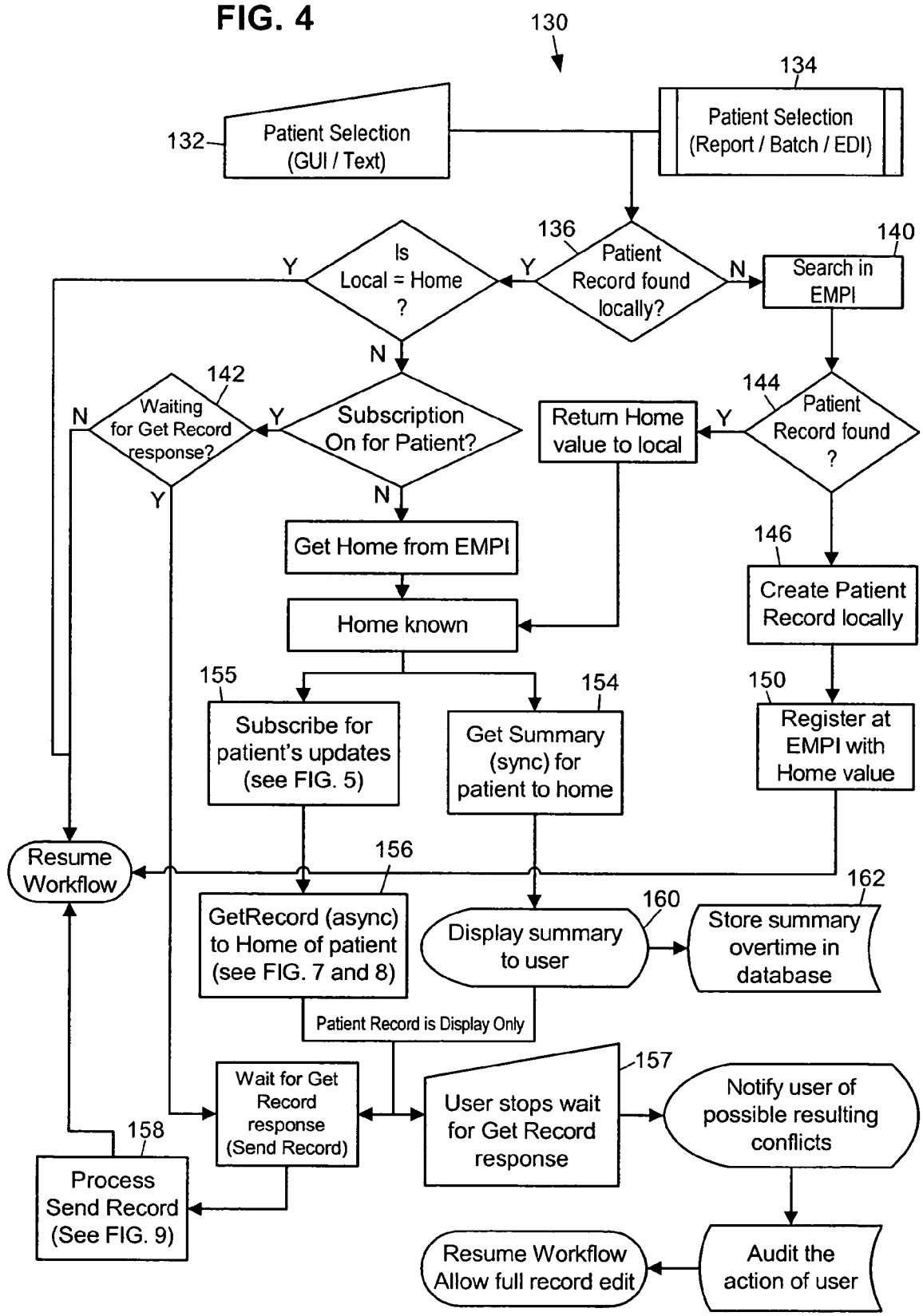
FIG. 4 is an exemplary flowchart representation of several steps that may be taken in identifying a patient.

FIG. 4 is an exemplary flowchart representation 130 of several steps that may be taken in identifying a patient and initiating the record pull process. In general terms, the steps illustrated in this flowchart provide a channel to share important information from a patient's medical record between various locations that are using separate information systems. The record pull process accomplishes this by allowing access to and use of patient record information at any location to help physicians and other personnel make sound clinical decisions about the patient's care. The record synchronization process ensures patient confidentiality and abides by the rules and regulations of the organizations exchanging data.

The steps in the patient record pull process are intended to run in a system such as that illustrated in FIG. 1, where there exists middleware adapter capability at every deployment 20-24 and 40-44 to process the outgoing and incoming messages. Messages are presented in an easily interpreted format, such as XML. This design assumes that the EMPI/EMFI deployment 40 houses the identifiable patient information needed to lookup patients across deployments. Messages to the EMPI/EMFI deployment 40 are sent through the middleware adapter 34 to query for patient record information.

A patient record pull may be requested when a deployment accesses a patient record not homed in that deployment. The EMPI provides the accessing deployment with the patient's home deployment so that it can request the patient record from the correct deployment. The requesting deployment is now a remote deployment with respect to that patient record. A summary of the patient record is first sent to the remote deployment while the full patient record is retrieved from the home deployment. At the time that the remote deployment requests the patient record from the home deployment, they are also subscribed to the patient record. This means that they may begin receiving all the updates, near real time, for the patient record as published by the home deployment.

Alternatively, a deployment may only subscribe to the data needed for a particular workflow. For example, a deployment may only subscribe for scheduling-related patient information, or registration-related patient information, thus increasing the data retrieval speed and lowering demand for system resources. A deployment may also choose to synchronize the entire patient record, but specify a period of delay for patient information that is not essential for a particular workflow.

Still referring to FIG. 4, the first step in patient record pull is to determine whether or not a patient has a different home than the current deployment. During a user workflow in an application, a patient record can be accessed via: (1) a patient lookup (block 132), (2) a report (block 134), and (3) a batch job that process patient records (block 134), for example. In the above cases, the deployment checks whether the patient's home deployment is the accessing deployment (block 136). The local Master Person Index (MPI) is searched for the patient. If the patient is not found at the local MPI then the EMPI is queried (block 140). The EMPI is also queried for the home deployment of the patient if the patient is found in the local MPI, but the current deployment isn't the home deployment for the record. The EMPI doesn't need to be queried for the home of the patient if the patient subscription is active. (If the patient subscription is active, it can be assumed that the local data for the patient record is current and up to date). Additional description of a patient record subscription is provided below.

If the EMPI doesn't find the patient at a block 144, then the user is able to create the patient locally (block 146) and register the record with the EMPI for use throughout the Community (block 150). Also, the user is able to assign a home deployment to the patient and update the EMPI with that information. If the EMPI does find the patient at block 144 and the patient record identification is successfully retrieved from the EMPI, then the Subscribe message is sent to the notification broker (block 155). Each deployment may have a global system for tracking all the patient records to which it is subscribed.

After the identity of a patient record is established and if the home deployment of the patient is not the current deployment, message requests are sent to the patient's home deployment to synchronously retrieve the patient record summary, "Get Summary", (block 154) and also asynchronously pull a copy of the full patient record to the remote deployment, "Get Record" (block 156). The home deployment for a patient record is stored as information in the patient record.

As mentioned above, after the identity of a non-local patient is established and if the record is not yet retrieved from the home deployment, the patient record summary will be requested from the home through a synchronous message (block 154). The patient record summary may be displayed to a user in display-only format (block 160).

This summary can be viewed by the user at the remote deployment to begin working with the patient while the full patient record is being retrieved through one or more asynchronous messages.

Furthermore, the summary may be time stamped and stored in the patient record for audit purposes. It may also be stored every time a patient summary is extracted from home (block 162), so that any clinical decisions made by a physician viewing the summary can be verified later.

While waiting for the patient record pull to complete, the user at the remote deployment may be allowed to perform certain actions on the patient record. For example, the user may be permitted to schedule an appointment or create a new event in the patient's record. For these actions to be performed, some of the patient data is present on the remote deployment in discrete format in the database and not as display-only. When a remote deployment sends a synchronous message to the home deployment, the response can include the additional discrete data elements. This section of the message response may be small in size, in order to ensure a quick response.

While the user is waiting for the response at the remote deployment, some functions on the patient's record may be unavailable. All the applications' functions can look at the server and see if the full patient record has been synchronized and whether to allow the users to start working on the record.

It should be noted that at the time of patient selection, if the full patient record is not synchronized the summary may appear. When the user opens such a patient record in any application, the user is allowed to perform relatively few actions against the patient record. Similarly, the user may be notified when the full patient record is synchronized and allowed to perform all the application activities.

If the user wishes to perform immediate actions instead of waiting for the full patient record synchronization, it is possible for the user to stop waiting for the response (block 157). In this scenario, the user actions may be fully audited and the data which is built by the user for the patient record is marked in conflict with the home deployment data. The system 10 may be restricted to al low only certain authorized users to perform this action. Also, the patient summary may be saved at the remote deployment and time stamped, so that it can be viewed later for audit purposes.

If the record pull is stopped 157, then the response messages of Send Record may be discarded and the update messages going to the home deployment for the new data may be marked as conflicting data at the home deployment. When a user stops the record pull for a patient record, the remote deployment is said to be in Local Activity Mode (LAM) for that patient. In this mode, the remote deployment discards any incoming update messages for that patient, but keeps sending the update messages of data collected at the remote deployment to the home deployment. When the same patient data is edited on different deployments, conflict between deployments can occur. Details of how the conflicts will be resolved and the various steps involved in this are discussed in the Conflict Resolution section below.

Still referring to FIG. 4, after it subscribes, the remote deployment sends the patient's home deployment a Get Record message to request the patient record, or portion of the patient record. Any existing data about the patient at the remote deployment, for example, earlier events at that deployment, is display-only at this point. The patient record is sent by the home deployment to the remote deployment asynchronously, in one or more logically affiliated Send Record messages. The remote deployment processes the Send Record message and allows the application to resume its normal workflow.

With regard to message affinity, the design of system 10 also ensures that multiple messages for record synchronization can be logically affiliated with each other to represent one action message. For example, the home deployment 20 can respond to an asynchronous Get Record message request by packing the patient record into one or more messages that comprise the Send Record message and process them together. Each message in this scenario includes a summary of the kinds of information in the other messages so that the receiving deployment knows what types of messages to expect. Although the messages are linked together for the goal of full record synchronization, these messages can be received and processed in any order. When sending the set of messages for the Send Record message, the home deployment can prioritize the type of data needed to be sent before any other data. A configuration setting allows a user to specify the order in which data groups are packed and sent. This means that high priority patient record information is sent immediately, so that users will have quick access to it.

Figure 5:
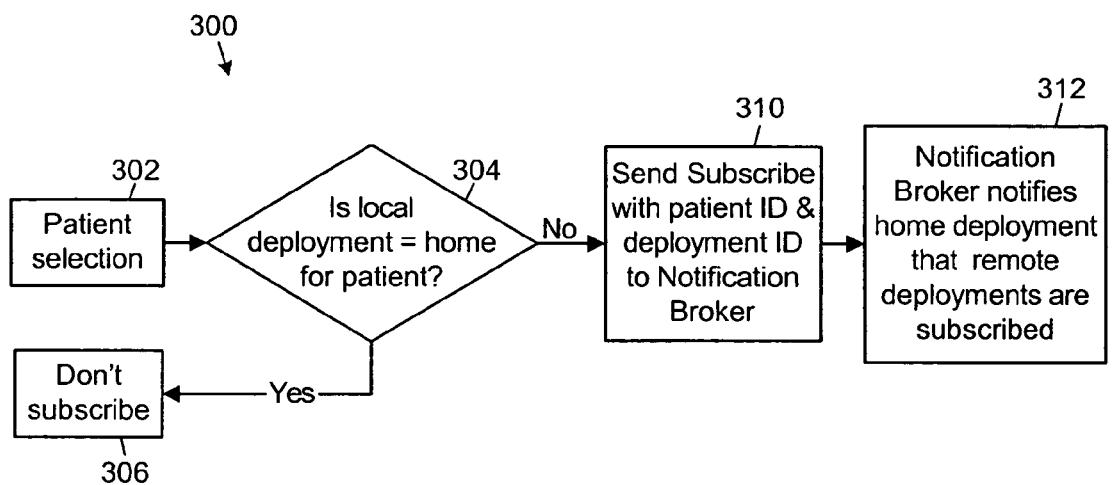
FIG. 5 is an exemplary flowchart representation of several steps that may be involved during the patient subscription process at a deployment.

FIG. 5 is an exemplary flowchart representation 300 of several steps used in the subscription process. If the remote deployment intends to edit the patient's record, then it subscribes to the patient's updates and the home deployment is updated with any changes it makes to the patient's record. When a patient is selected (block 302), the system checks to see if the patient is homed on the current deployment (block 304). If it is determined at the block 304 that the local deployment is the home for the patient, the software does not cause the remote deployment to subscribe to the record (block 306). If it is determined at the block 304 that the local deployment is not the home deployment for the patient, the system causes the remote deployment to send a Subscribe message, including the patient ID and home deployment ID, to the notification broker 44 (block 310). The notification broker in turn adds the remote deployment to the list of recipients for updates made to that patient's record. The notification broker also notifies the home deployment that a remote deployment is subscribed, and that it should keep the community updated with changes. This is used to optimize the publishing of updates from the home deployment. The updates are not sent if there are no remote deployments subscribed for that patient's updates. The home deployment for the patient record then publishes the patient record changes for the community.

The home deployment for the patient record may be directly notified by the remote deployment whenever it modifies the patient record (block 312). This is important for effective conflict resolution and stepping up and down between software versions. The home deployment may publish the record updates to the Community through the notification broker 44, and all the deployments that are subscribed for the patient's updates receive the published message. The notification broker 44 is responsible for notifying each deployment of all active subscriptions for the patient records homed at that deployment.

Figure 6:
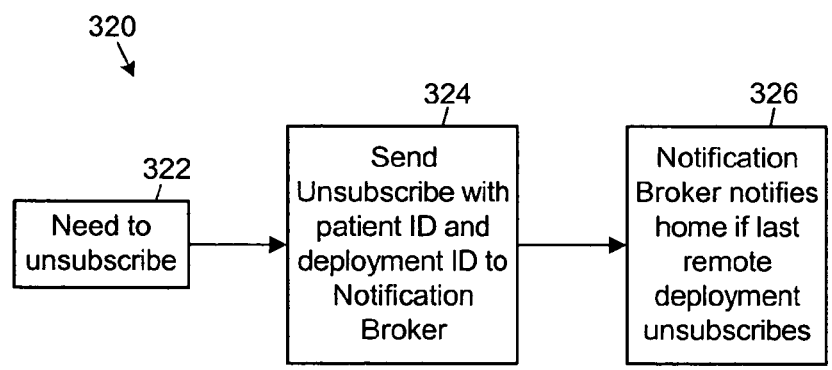
FIG. 6 is an exemplary flowchart representation of several steps that may be involved during the unsubscribe process for a patient record at a deployment.

FIG. 6 is an exemplary flowchart representation 320 of several steps used when closing a subscription, the "unsubscribe" process, to a patient record. When a remote deployment no longer requires updates to a patient record, such as when the patient is no longer receiving care at the deployment, an Unsubscribe message is sent to the notification broker with the patient ID and home deployment ID.

While accessing the patient record in an application workflow, the user may perform actions that trigger the deployment to unsubscribe to the patient record, and stop receiving updates published by the home deployment. Examples of such actions are closing (finalizing) an outpatient encounter or discharging a patient. When a need to unsubscribe has been identified (block 322), an Unsubscribe message is sent to the notification broker 44 to remove the remote deployment from the recipients list for the patient's updates (block 324). If this is the last remaining remote deployment subscribed to the patient record, the notification broker 44 then notifies the home deployment that remote deployments are no longer subscribed to the patient record and that there is no more need to publish updates 326.

Now, if users at the remote deployment wish to modify the patient record through some functions in the application, then the remote deployment has to pull the record of the patient again from the home deployment and start a subscription.

A configuration setting at each deployment may determine the default number of days that subscriptions are kept open for a patient record or portion thereof after a user commits an action to cancel subscription for a patient's updates. When the user commits an action that causes a subscription to be canceled, the subscription may instead be kept active for that predefined period of time. This is helpful, for example, for encounters and admissions for which charges are entered nightly. For administrative purposes, there may be a tool to explicitly start and end subscriptions for a patient's updates. As mentioned above, if a Subscribe message is sent for a patient from a remote deployment, then an implicit Get Record message may also be sent to the patient's home deployment.

Figure 7:
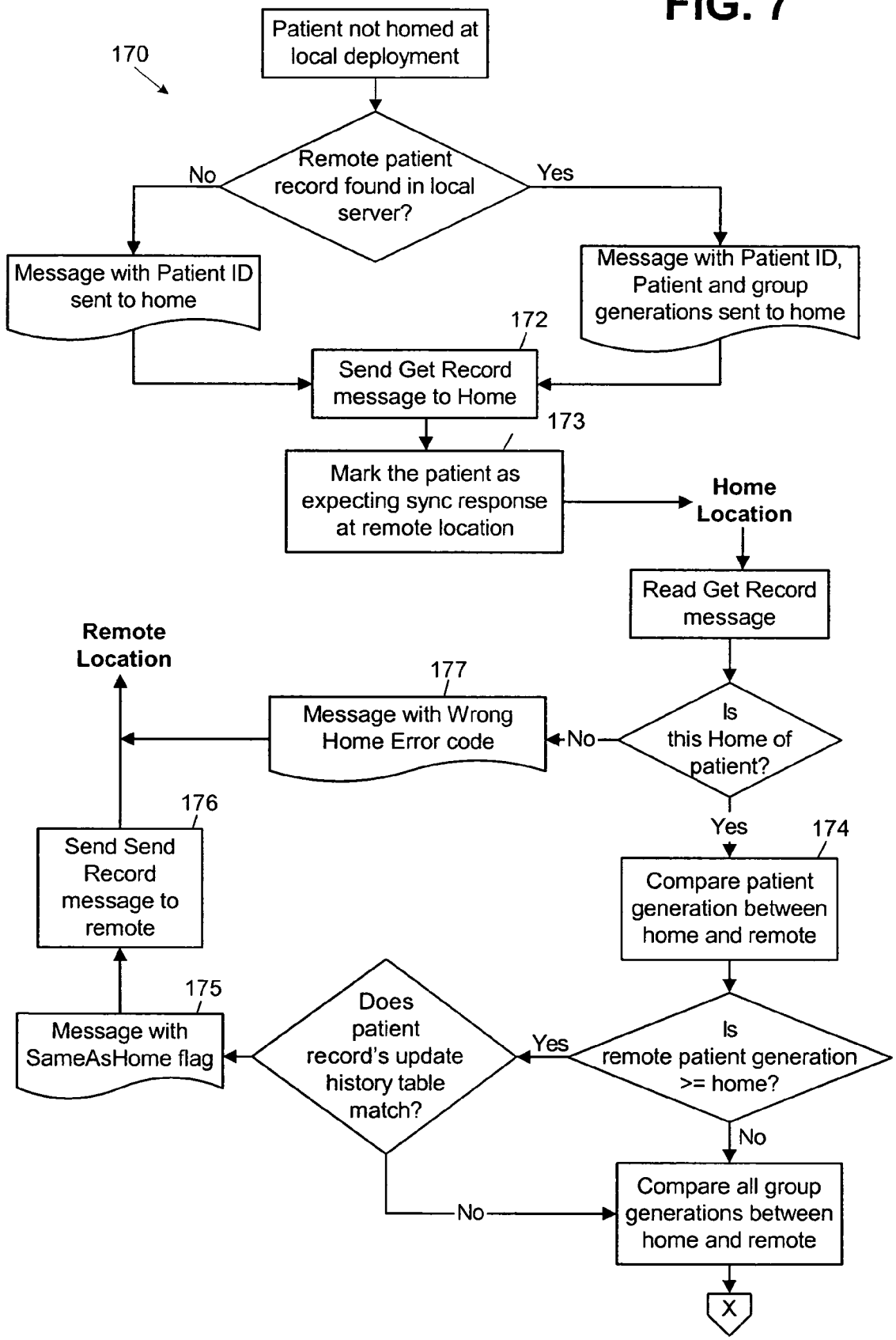
FIG. 7 is an exemplary flowchart representation of several steps that may be used in pulling a patient's electronic medical record from the record's home deployment to a remote deployment.
Figure 8:
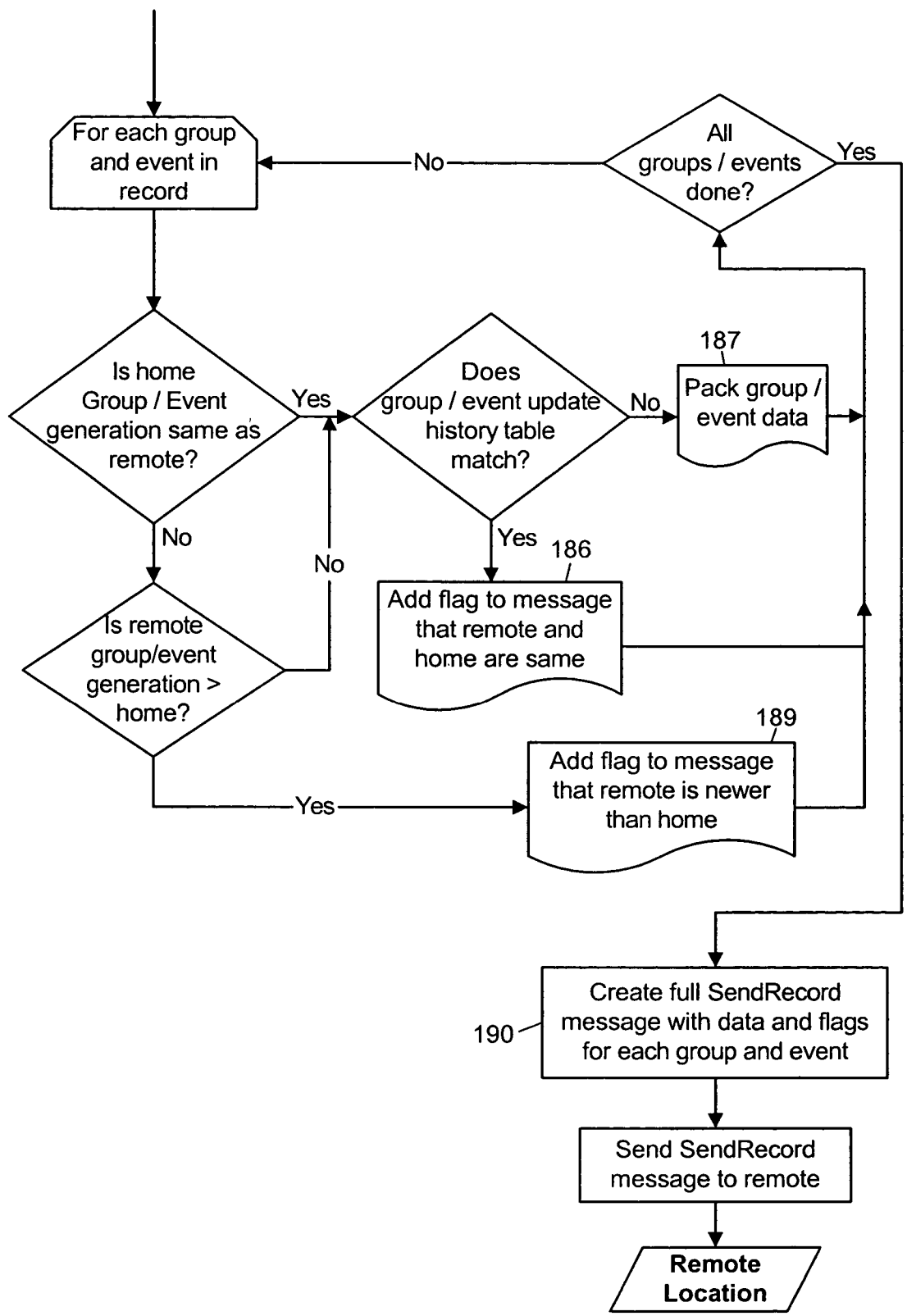
FIG. 8 is a continuation of the exemplary flowchart illustrating more actions used by the home deployment when sending a response to a remote deployment's request for a patient record.

FIG. 7 and its continuation, FIG. 8, is an exemplary flowchart representation 170 of several steps used in synchronizing a patient's existing electronic medical record, whether it exists in out-dated form or not at all at the remote deployment, with the record's home deployment. As described above, the remote deployment requests the up-to-date patient record from the patient's home deployment by sending a Get Record message (block 172) to the home deployment.

When a Get Record message is sent by a remote deployment, a deployment-side setting is marked at the remote deployment with the patient ID, signifying that a response is expected for this patient's record pull request (block 173). This setting is used to filter any unsolicited messages and also to notify the user at the remote deployment that a patient's full record pull is in progress.

When the Get Record message is received, the home deployment first confirms that the patient is homed at that deployment. If the Get Record is sent to the wrong deployment, then the system may return a Wrong Home Error code (block 177) message back to the requesting deployment.

Once it confirms that the patient is homed at the deployment, the system then compares the records and sends any new information for that patient record at the home deployment to the remote deployment in a Send Record message.

Figure 10:
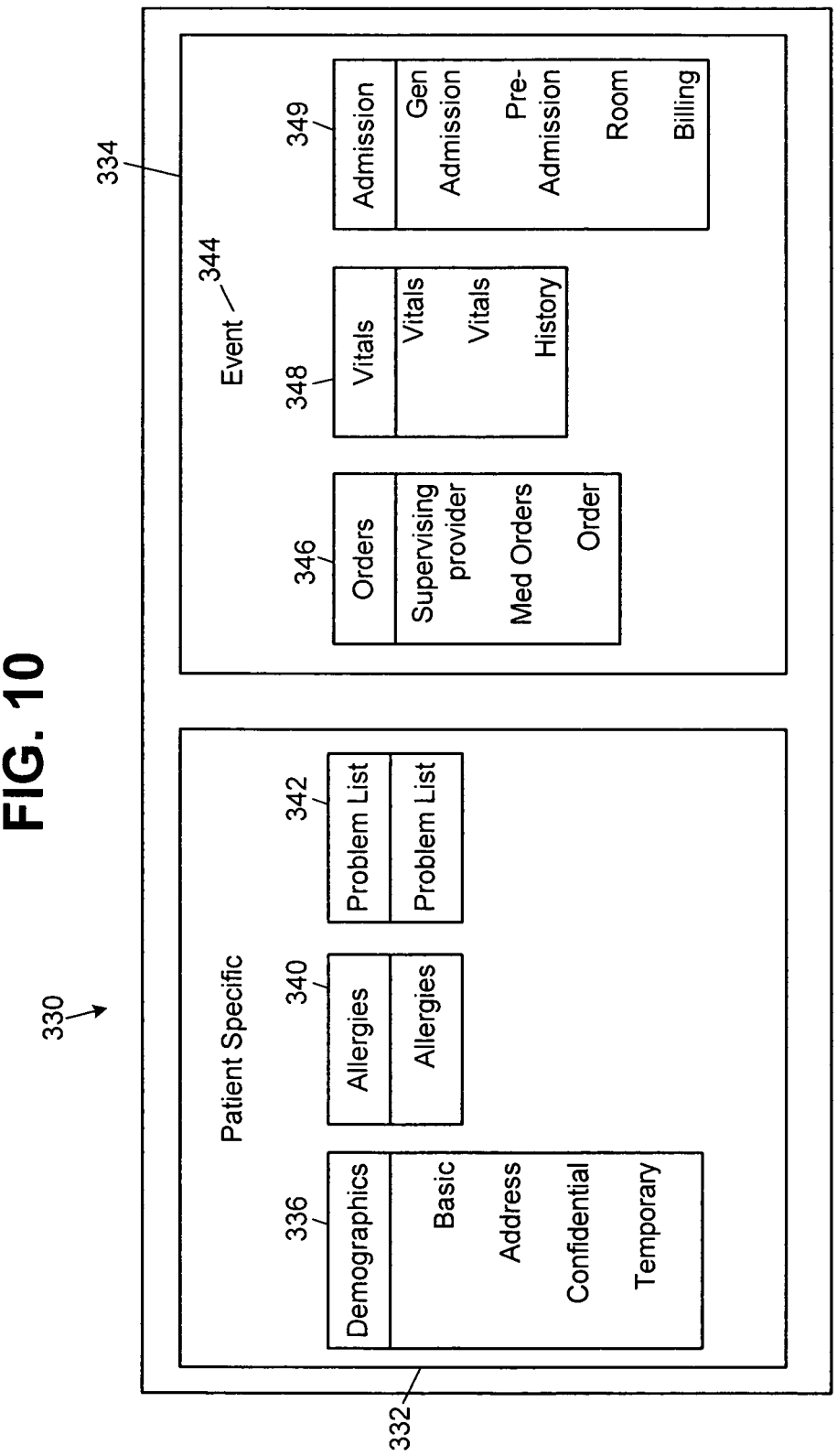
FIG. 10 is an exemplary block diagram illustrating the hierarchy within a patient record with a small set of clinical data groups and leaf groups.

Because the patient record can exist simultaneously at multiple deployments, the system 10 keeps track of the most current data for that patient record, including the updates and iterations of updates made to the record. For the purposes of record synchronization, the patient record and all the related data is divided into hierarchical groups of data. FIG. 10 is an exemplary block diagram 330 illustrating the hierarchy within a patient record with a small set of clinical data groups and leaf groups.

A reason for creating hierarchical groups of data is that data grouping enables the system to locate, package and send only the changed portions of records instead of the whole record which facilitates performance optimization. Other reasons are that data grouping makes it easier to search for changes in a patient record, and conflicts between multiple deployments updating the same patient record are minimized as a result of data grouping because in many cases the deployments will not edit the same portion of the record at the same time. Thus the home deployment can smoothly compare and merge the updates it receives. Auditing changes at the more granular data element level may provide another method of achieving the same need.

The exemplary patient record of FIG. 10 is made up of: Store-Once patient specific data groups 332, patient record events 334, and Event Data groups. Examples of Store-Once data groups are: demographics, allergies, problem list 342, and patient preferences. Examples of patient events are: encounters 344, admissions, and appointments. Examples of Event Data groups are: orders 346, vitals 348, admission data 349, and appointment resources.

Each of the Store-Once and Event Data groups may be further divided into smaller leaf groups which contain a number of data elements. Examples of leaf groups are: Demographics Name, Demographics Address, and Demographics Temporary Address. Some of the conventions for defining a leaf group are: defining a leaf group to have only one type of data, either Store-Once or Event Data elements; defining a leaf group to have multiple parents, and requiring a data element to belong to only one leaf group.

Data elements within a leaf group can point to dynamic database records. Dynamic database records are created as part of patient workflow in various applications and are synchronized between deployments with the patient synchronization messages. To transfer the dynamic database records along with the patient record, the dynamic databases are also divided into a hierarchical group structure. Generation levels may be assigned to dynamic database records too. Any changes to a dynamic database record's group may be propagated to the patient record and eventually increment the patient generation.

In order to track changes to a patient record, search for changes within a patient record, and compare the same patient record across deployments, both the patient record itself and its individual groups and events are marked with generation levels when they are modified. Generations are assigned to events so that a particular encounter can be synchronized and compared easily. Each version, or generation, of a group is tracked. When a change is made to a piece of data in the group, the generation is incremented, thus flagging the group as requiring synchronization. Each level in the hierarchy in the patient record is assigned a generation and is incremented if any of the child groups or data elements are edited. In this manner, the system 10 avoids having to send the entire patient record every time a change is made to one part. This concept is discussed in more detail below. Every patient has a generation level 1 when it is published the first time into the Community and it is updated to the next generation level when the record is published.

Along with the generation for the patient and the groups, the history of the updates from various deployments may also be stored. The update history of the patient record or the group tells us the foundation on which the data group was built. This is important information when update messages are processed and during conflict detection and resolution, described in later sections.

Each group may contain several special fields with metadata. These fields include, for example: generation (the latest iteration of a group); changed flag (a Boolean flag indicating that a group has changed since its generation was last incremented); generation instant (a time and date indicating when the generation was last incremented); and update history (a table holding the ID's of the deployments that have contributed to a group and the last generation each deployment contributed).

In addition, the top-level group for a record may have an additional number of fields. These may include, for example: Last Generation Published (LGP) (indicates the last generation any deployment has published to the Community); and Update Processing Record (UPR) (flag indicating that an update for this record is currently being processed and sent out).

The design of system 10 provides a schema definition to represent data groups for a patient's record which includes generation information about each data group, as well as dependable and identifiable representation of data pointers for static master file records, dynamic database records, lookup table values and events. This schema is used to create messages to synchronize patient records across deployments.

The remote deployment which wishes to retrieve a patient's record from the home deployment for that patient, sends a Get Record message to the home deployment (block 172) along with the patient record's and individual groups' generation level information. The remote deployment may send the following identifying information in the Get Record message: the intended receiver (patient's home deployment), the patient ID, the patient record generation and update history (FIGS. 12 and 21 discuss update history in detail), the group hierarchy and each group's generation and update history, the remote deployment's system software version (used for stepping up or down the data in the message format), and the event present at the remote site and its generations and update history with its groups' generations and update history (This may not be true for patients synced for the first time to the remote deployment).

Because the Get Record message is requested asynchronously, it is added to a queue to be processed by the home deployment and when it is, the Send Record message is sent asynchronously to the remote (block 176 of FIG. 7 and block 190 of FIG. 8).

The home deployment first compares the generation levels of the patient record on its own server to the generation level sent inside the Get Record message (block 174). The Send Record message (block 191 of FIG. 8) contains information regarding each group and event in the patient record with its compared info. If the generation information on the remote deployment's patient record is lower (older) than that on the copy at the home deployment, a flag indicating that home has newer generation data than remote (block 186 of FIG. 8) is added to the Send Record message. The new data and its generation levels are packed and sent to the remote deployment (block 191 of FIG. 8).

If the generation information on the remote deployment's patient record is equal or newer to that found on the home deployment copy of the record and if the update history matches, a flag indicating that the remote has the same generation of data or higher as the home deployment (block 175 of FIG. 7) is added to the Send Record message.

If the generation information on the remote deployment's patient record is equal or newer than that found on the home deployment copy of the record, but the update history does not match, then the home deployment compares all group and event generations and if the group or event generation of the remote deployment's copy is greater (newer) than the home deployment, a flag indicating that the remote has newer generation data than the home deployment (block 189 of FIG. 8) is added to the Send Record message.

Figure 9:
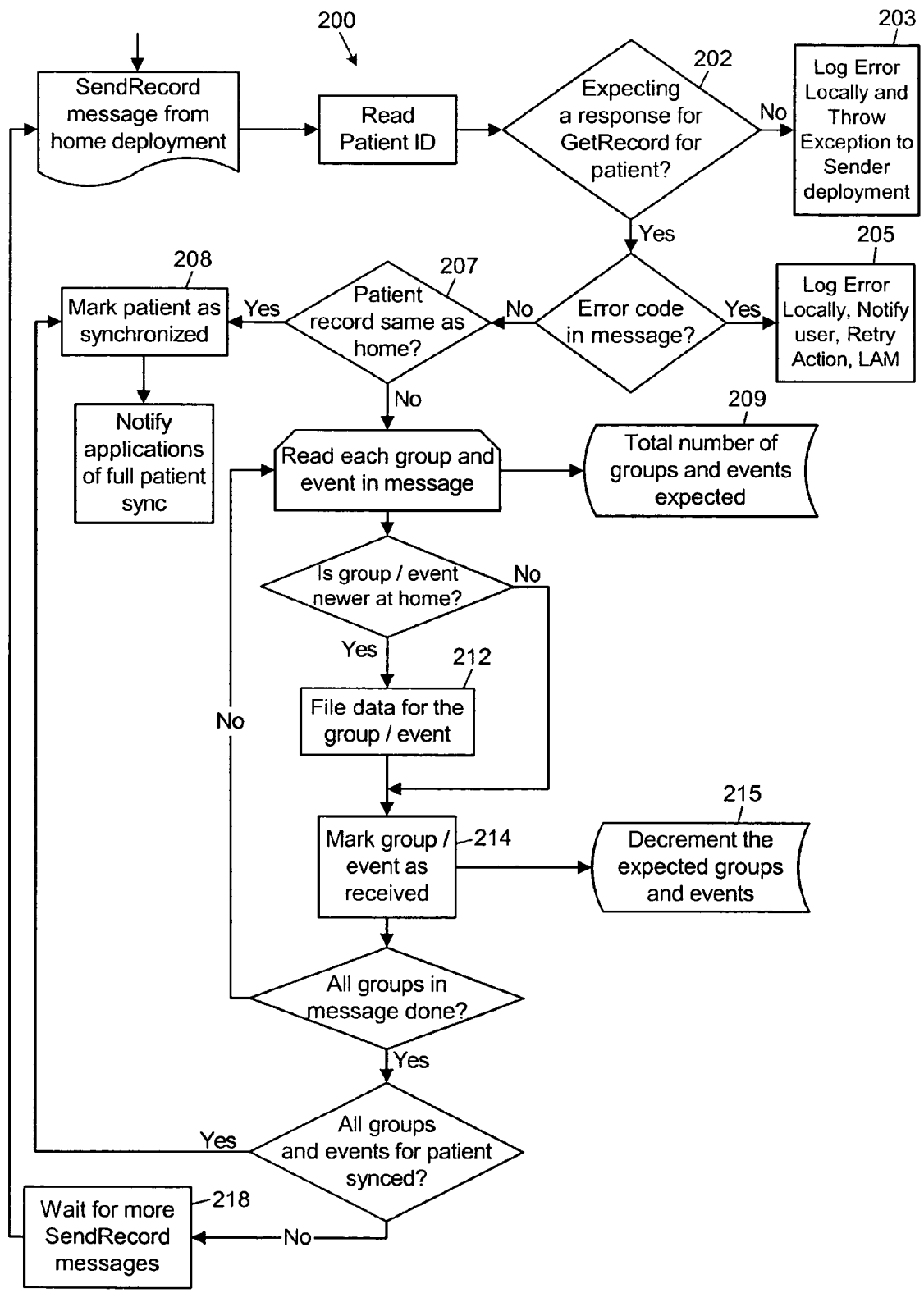
FIG. 9 is an exemplary flowchart representation of several steps that may be used when a remote deployment processes a patient record it received from the home deployment.

FIG. 9 is an exemplary flowchart representation 200 of several steps taken by a deployment when it receives and processes a Send Record message. The Send Record message may include, for example, the following information in the message: the intended receiver (remote requester), the patient ID, the patient record generation and update history with flag of the difference in generation for the record (as mentioned above), the group hierarchy and each event or group's generation and update history, with flag of the difference in generation for the group or event, the discrete data for each group with, for example: static master file pointers, dynamic master file pointers, event pointers, lookup table pointers.

If needed, the Send Record message can be broken into smaller messages to keep the size manageable. Each of the messages may include some important identifying information in the header. The header of the message (or each message, in case there are multiple messages for the response) may have the number of groups and events that exist in the patient record that would be part of the message(s). For example: the patient ID, the intended receiver (remote requester), the total number of events for the patient and total number of groups, which event and groups this message contains. This information can be used to help users keep track of the progress of the patient record synchronization process.

For optimization, the processing of messages may be shared between the production and the shadow server at any deployment. A Get Record message may be sent out by the production server of a remote deployment and received by the production server of the home deployment. The response message Send Record is created and sent by the shadow server of the home deployment. On the remote deployment the Send Record message is received and processed by the production server.

By looking at any of the messages, the remote deployment can tell how many of each group to expect for the patient record. As the remote deployment gets more messages, the deployment unpacks each group, marking the group or event "received." When all the messages for the set of Send Record messages have been received, the data in the groups is filed in the patient record. This way the remote deployment can at any given point tell how much of the patient's record has been received. The unpacking of messages and filing of the data is discussed in more detail below.

When the remote deployment gets the first message in the Send Record message set, it stores the total number of groups of Store-Once data elements, the total events, and the total number of Event Data groups in a deployment-wide setting.

As mentioned above, the remote deployment keeps track of the amount of data received per patient in the record pull process through the number of groups and events, and once all the groups and events for the patient are received from the home deployment, the data is filed in the patient record and the patient record is marked as synchronized. At this moment, the applications are notified and patient functions become accessible to the user.

Still referring to FIG. 9, when the remote deployment receives the Send Record message from the home deployment, it reads the patient ID and checks to see if it was expecting a response for the patient (block 202). If it was not expecting a response for the patient, an error is logged locally and an exception is sent to the deployment that sent the Send Record message (block 203). If the remote deployment was expecting a response but an error was found in the message, an error is logged locally, the sending deployment is notified, and the user at the remote deployment is allowed to proceed in Local Activity Mode (LAM) (block 205). If the patient record information is the same as that sent from the home deployment (block 207), the patient is marked as synchronized (block 208) and the user at the remote deployment can proceed to work with the patient record fully.

If the patient record received from the home deployment in the Send Record message is not the same as that on the remote deployment (block 207), the remote deployment reads the Send Record message and counts the total number of expected groups and events (block 209). If the incoming message contains groups or events that are newer than that stored on the remote deployment, the new information is filed (block 212). If the incoming message contains information that is older than that stored on the remote deployment, it is not filed. Generations and the update history table are used to determine which information is newer. Each group and event is marked as received (block 214). As this is accomplished, the count of expected groups and events is decremented (block 215). When all groups and events are done, the system checks if all groups and events for the patient are synchronized; if they are not all synchronized, the system waits for more Send Record messages (block 218). If they are, the patient record is marked as synchronized (block 208), and the user is able to continue working with the patient record (block 209).

FIG. 11 illustrates an exemplary update history table for a Demographics Group of a patient record. As previously mentioned, records include a set of information referred to as the record's update history. Throughout this patent, examples used will illustrate the update history using a table that details, for a group, the deployment and generation that contributed to the current state of the group. In the table header 350, 115781 is the Community ID for the Patient database record being summarized; Demographics indicates the data group to which the table refers. The table lists five deployments in the Community: A, B, C, D and E. The data group Demographics has been updated five times by various deployments in the Community to arrive at generation 5 which was last updated by deployment B. The current generation of the Demographics group, which is the last update generation received or published for the group is generation 5.

The update history shown in FIG. 11 tells us that the patient was created at deployment A and the Demographics group was updated by deployment E to generation 2, by deployment D to generation 3, by deployment C to generation 4 and then finally by deployment B to generation 5. Generation 5 is the last updated generation of the group, thus it is stored in the current generation field for the Demographics group.

The current generation and update history information of the patient record, data groups, events and dynamic database records may be stored along with the patient record. The group information is stored as part of the database schema for the patient record.

When packing the data groups for a patient's record at the patient's home deployment 20 all the patient specific Store-Once groups are packed first followed by the Event Data groups. The Event Data groups are prioritized by a configuration setting which determines the number of days in past or future to search for events. These events are packed first, before the rest of the events that are part of the patient record. Examples of default behavior may be to process: events for 30 days in past, events for 30 days in future, all past events, and all events for future. As previously mentioned, each message header may include the correlated information about other messages which contain the rest of the event groups for the patient record.

For the purposes of this discussion, a tightly affiliated community is assumed. However, different levels of affiliation and data sharing amongst deployments are possible. The deployments participating as a Community can agree to share certain patient data during the record synchronization process, but due to some legal or contractual reasons, they might not agree to share other data. There may be a setting per deployment to filter incoming or outgoing messages depending on these contracts or agreements. Some of the requirements for these settings may include: (1) Deployment settings at each database level of which data groups can be sent out as part of a record synchronization message and (2) Deployment settings at each database level of which data groups can be accepted when receiving a record synchronization message.

In a loosely affiliated community, a few levels of synchronization are possible, including, for example: Central Home, Distributed Home, and Distributed Home with Focal Point Server. For a community using the Central Home synchronization level, the whole patient record resides on the patient's home deployment and is sent to the requestor from that deployment when a Get Record request is made. It works similarly to the tightly affiliated community.

For the Distributed Home synchronization level, only a part of the patient record is stored on the home deployment because of certain non-sharing rules between deployments: Various pieces of the patient's data are owned by various deployments. When a remote deployment requests a patient's record, it requests the home deployment for the patient and returns only the data owned by the home deployment. The data residing on the other remote deployments is not sent to the requesting deployment.

In a loosely affiliated community, if there is no EMPI present for patient records, then each deployment publishes each patient to the Community with identifiable information at the time of creation. MPI tables are created in each of the deployments to resolve the patient record. When a deployment publishes a new patient record, the receiver marks the sender deployment as the home deployment for the patient.

If there is no EMFI present for static master file records, then each deployment may need to publish changes to static master file records and selection lists nightly to the other deployments, using the Master File Index (MFI) and Master Category Index (MCI) techniques to resolve the pointers. Another technique is to use the Active and Passive snapshots describe below to synchronize the static master files and lookup table values.

Data Mapping

Figure 12:
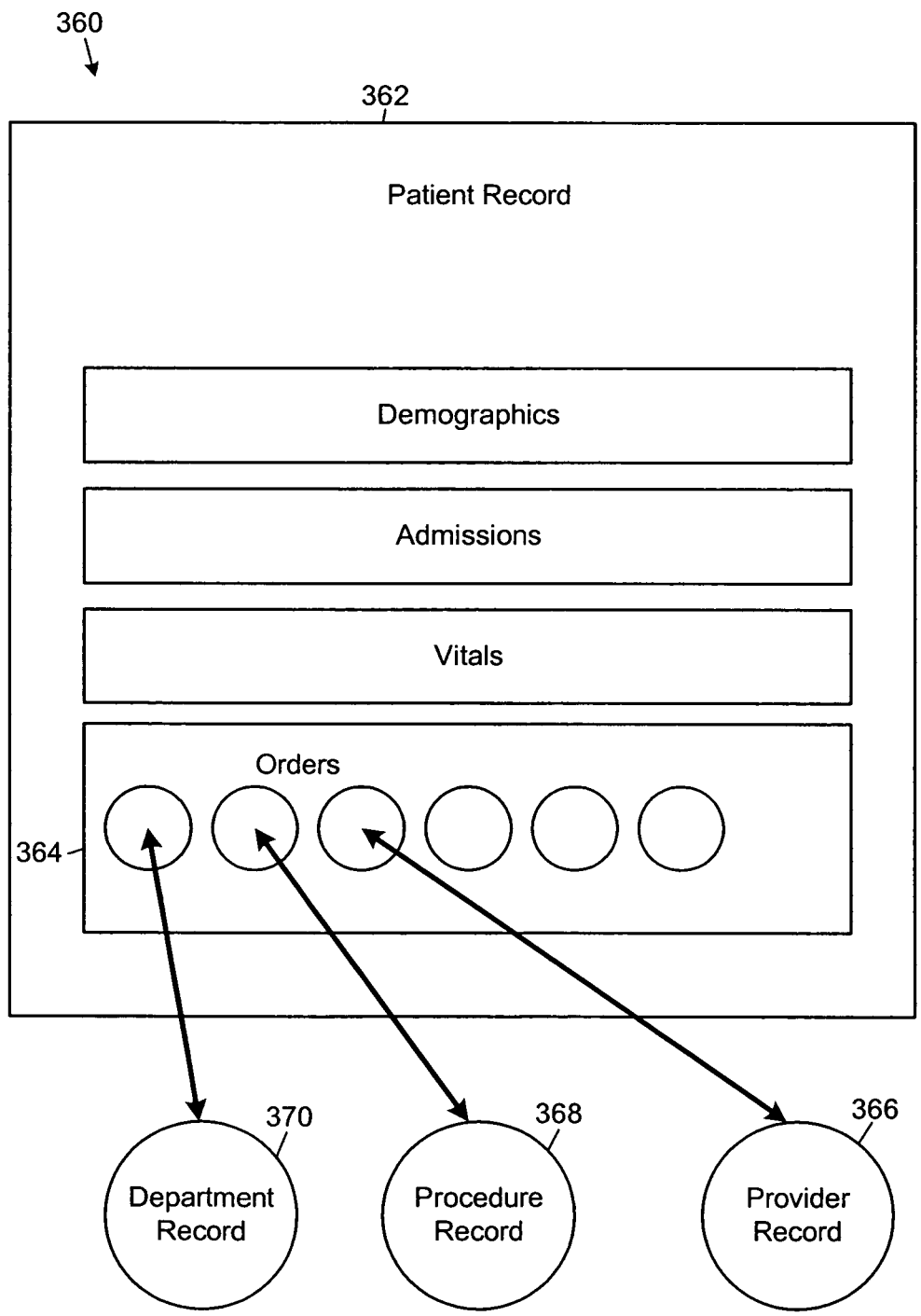
FIG. 12 is an exemplary block diagram illustrating a patient record with pointers to external data.

When a patient record is synchronized to another deployment, there are various data elements in the patient record—typically pointers to other records or selection list values—which simply cannot be resolved in the receiving deployment, or have pointer values that need to be translated for use at the receiving deployment. For example, FIG. 12 illustrates a block diagram 360 of an exemplary patient record 362 with pointers to external data. As shown in diagram 360, an orders section 364 in the patient record 362 includes pointers to external data in: a provider record 366, a procedure record 368, and a department record 370.

In addition to reconciling pointers between database records, there will be deployment-to-deployment variations in some selection lists, and these pointers need to be reconciled as well. A "selection list" data value is an entry which is restricted to a limited list of possible answers. For purposes of this discussion, each possible choice in the selection list is composed of a selection list ID (a unique identifier within the list, typically numeric), and a selection list value (the value that the end users will normally see, typically a text value). For example if a data value is restricted to choices of "Yes" or "No," that would normally be represented as a selection list with two possible choices on the list: 1—Yes and 2—No. In this case "1" is an example of a selection list ID, and "Yes" is an example of a selection list value.

Several techniques may be used to resolve the various data pointers. During patient synchronization, deployments should be able to determine which technique to use to resolve various data pointers within the patient record. These techniques can vary depending on the type of data and the deployment. For events, the technique used should be specified for the database to which the event belongs. For static master file records and dynamic database records, the techniques used for resolving each of the records should be specified for each database. For example, the technique used to resolve data pointers for provider records can differ from that used for order records. For selection lists, the technique used to resolve the data pointers should be specified for the selection list data element. Other data elements pointing to the same selection list use the same technique for resolving data pointers.

When synchronizing a patient record that includes pointers to static master file records, steps should be taken to ensure that those static master file records are either already present on the other deployment or created on the receiving deployment as a part of the synchronization operation. Some techniques assume that static master files records are always present on receiving deployments, and thus require that the system build process ensures that all the deployments get copies of records whenever they are created in the community. Remember, these are records which are usually very static in their life span and generally are created as part of the initial system and software setup through an administrative action. Examples of these are provider records, procedure records and employee (user) records.

Figure 13:
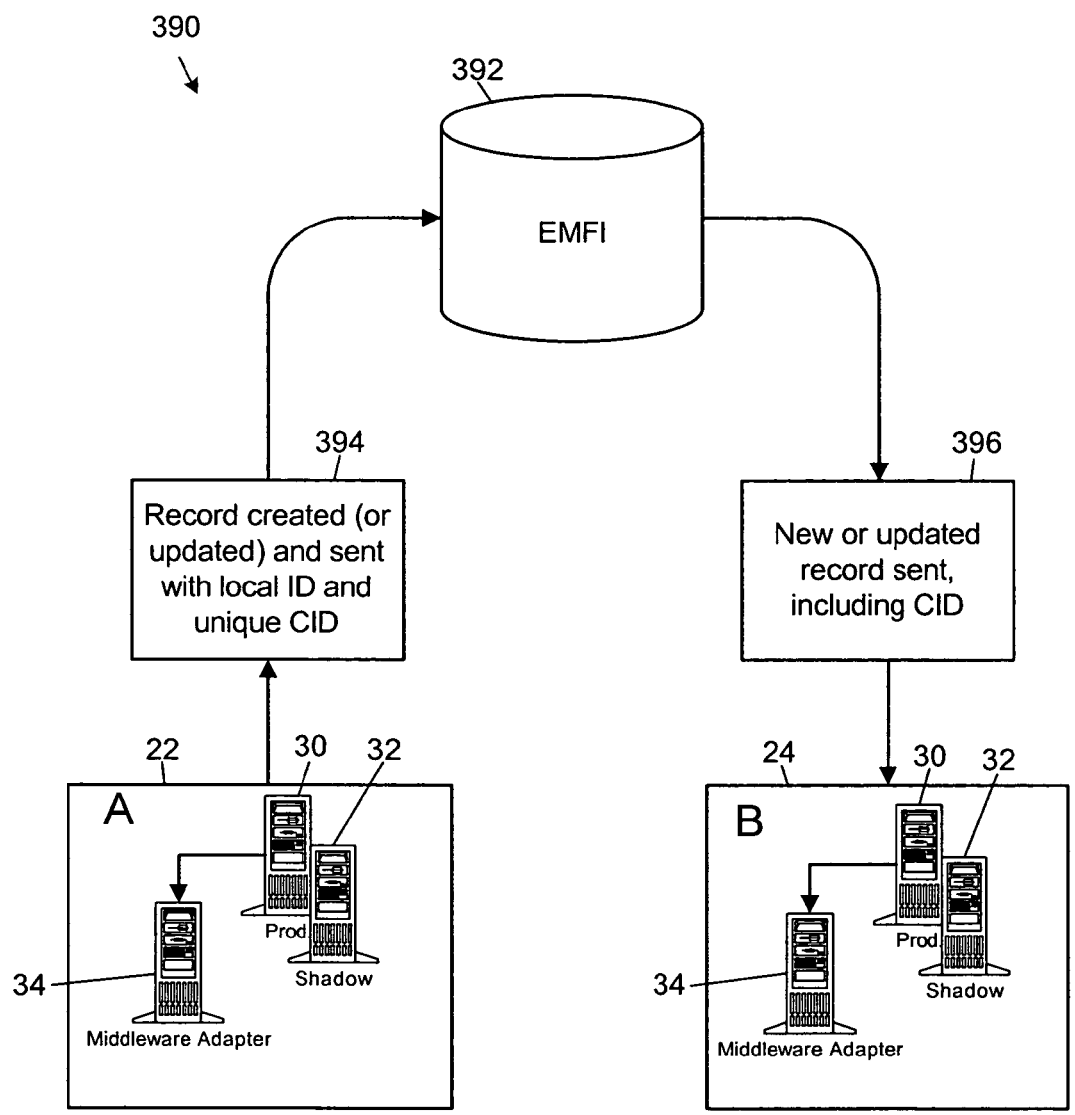
FIG. 13 is an exemplary flowchart representation of the steps that may be used when publishing a record via the EMFI.

FIG. 13 is an exemplary block diagram 390 of a community record publication process. In this technique, there may be a central hub to assign a Community ID (CID), unique across all deployments, to each static master file record. This central hub, also called the EMFI (Enterprise Master File Index) 392, keeps track of all the static master file records in the Community and the CIDs of each. When Deployment A (block 22) creates a new static master file record (block 394), such as a new provider record, it is sent to the EMFI which assigns a CID to the record before sending the new record (block 396) to Deployment B (block 24). Depending on the Community's choice of method to resolve pointers, Deployment B may the assign the new incoming record a separate, local ID in addition to the CID that the EMFI sent with the record.

In communities where static master file records are either present on the other deployments or copied to the other deployments when they are created, there are two ways to handle resolving a patient record's pointers to static master files: Direct ID Match and a mapping technique.

If the participants of a community choose to use the Direct ID Match technique, the system build may require that the static master file records in the Community have mutually identical ID generation mechanisms so that the same record ID is used for the same record across deployments. This technique is very efficient when pointers in the patient record are being resolved because no special mapping is required to translate the data, the use of CIDs unnecessary.

If the community participants agree to use a mapping technique, then individual deployments in the Community may have their own local IDs assigned to a record and the resolution at the time of patient record synchronization may map the static master file records by one of the following exemplary methods: Community ID, Combination of fields matching, and Embedded Master File Index (MFI) table.

Figure 14:
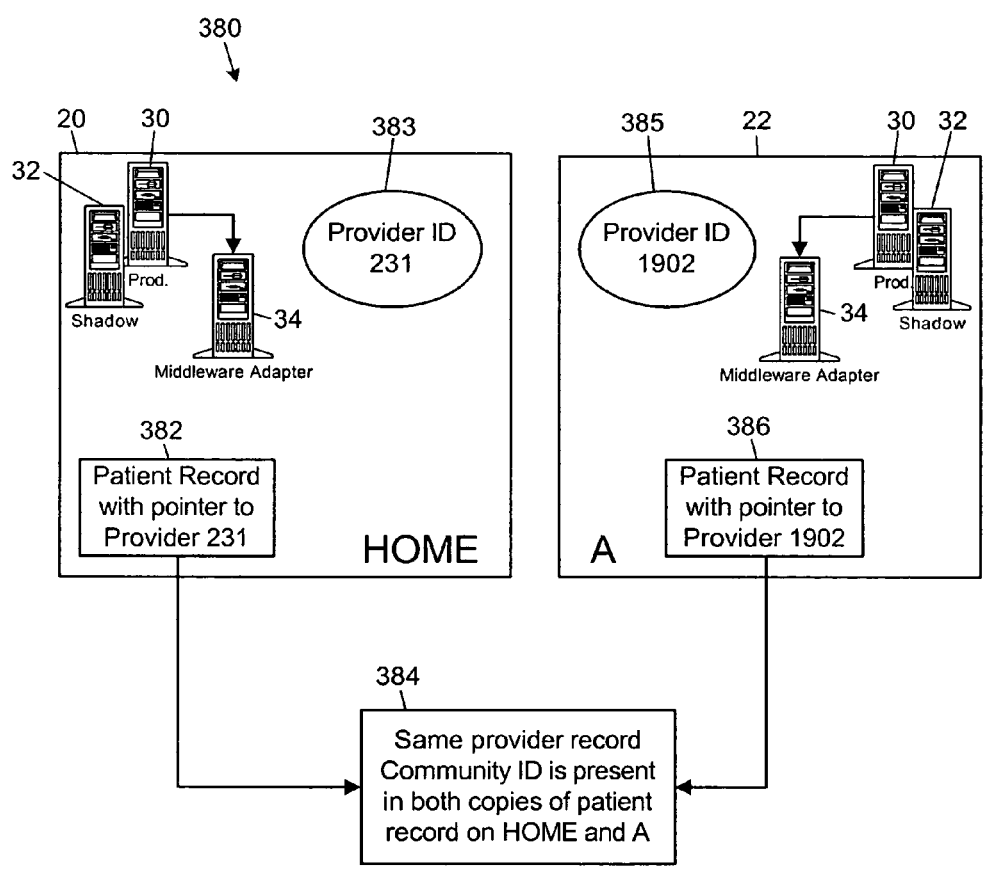
FIG. 14 is an exemplary block diagram illustrating a mapping technique involving a Community ID.

FIG. 14 is an exemplary block diagram 380 of the Community ID technique of mapping static master file records. At the home deployment, a provider record was created with a local ID 231 (block 383). When the provider record was created, it was also assigned a unique Community ID (FIG. 13, block 392), which was communicated to both deployments. The patient (block 382) receives care from provider 231, and the patient record now contains a pointer to this provider record. The provider offers care at both deployments. At deployment B, however, the provider record has a local ID 1902 (block 385).

When the patient record is synchronized, the data pointer in the record 382 from the home deployment (block 20) points to the provider record 231 on the home deployment (block 383). This provider record may also contain a CID that the receiving deployment A (block 22) may use to "map" the record to local provider record 1902 (block 285) thus resolving the patient record pointer (block 386.)

In the technique involving combination of fields matching, the participating deployments may agree on matching certain static master files using a combination of fields within the record. For example, the provider record could be matched using the SSN, Tax ID, Name and Address. So, within the message containing the patient data, the additional information to identify the provider record is included.

In the technique involving the embedded MFI table, the static master file records are mapped across deployments using a table of cross deployment IDs for each record. For every record, each deployment keeps a table of IDs for that record in other deployments. That table is sent as a part of the synchronization message, and the pointer is resolved during the filing process.

In all the above techniques there may be a way of publishing the static master file records' changes to the Community. This may be done either through a central hub—the EMFI, or through periodic imports of records to individual deployments, which could include nightly imports.

Because each deployment receives published static master file records from all the other deployments, a deployment has the option to inactivate, or "hibernate," each record. Also, a deployment can keep local autonomy by modifying certain sections of the record to fulfill local needs.

Many of the above techniques may be useful for tightly affiliated communities where there are agreeable terms and conditions for building the system collaboratively.

In the case of loose communities where there are no agreements to build the system collaboratively, the following techniques may be used: snapshot and no resolution. The snapshot technique involves including identifiable information for the static master file record in the patient synchronization message so that the receiver can create the record at the time of synchronization to resolve the pointer. The next time the deployment receives the same static master file record, it can match the record by either using the combined fields matching technique or the MFI table technique. In this case the Community won't need to publish the updates of records created in a deployment.

There may be two types of snapshots: passive and active. A passive snapshot means that the sender is unwilling to send more information for the static record. An active snapshot means that the sender is willing to share more information about the static record, if it is requested. A flag within active snapshots may tell the application to provide users with a tool enabling them to request more information about the static record if needed. The additional information allows the record to be fully viewed or even used on the other deployment.

Records received via snapshots may be added to a queue to be processed by an administrative tool that can execute the following procedures: mark a record as inactive, change local settings for a record, request additional information for a record from owner (if active snapshot). If the participating deployments are not willing to share certain types of static records, then the last resolution option is to always point the field to a temporary "Other" record, which lets the user know that the data is insufficient. If for certain reasons there is no "Other" record for a static master file, the data pointer may not be resolved and the record may be added to a queue to be handled by a business process.

The types of techniques to be used for various static master files on a deployment may be configurable in the community global setting. At the time of filing incoming messages for patient record synchronization, the settings are referenced for resolving the data pointers correctly. The settings are dependent on the affiliation levels across the deployments when building the static master files. The type of technique to use to resolve a master file's records can also vary between regions within an organization.

Some of the techniques discussed above require that the records for all databases are always present at every participating deployment for the resolution to occur successfully. This can result in some unexpected behaviors by other applications. For example, on each deployment, when the user searches for a static master file record, the selection list may display all of the static records across the community, including those belonging to outside deployments. Also, record processing could be affected: The application code that processes data for all static master file records in a deployment may process the data for all other deployments too. This can result in unexpected behavior and some performance implications.

These problems may also exist for techniques that require static master file records to be created on the fly, as they are during patient record synchronization using a snapshot, because the number of records will grow larger and larger. This scenario calls for a method of storing the "out of deployment" static master file records in a format in which they can be easily referenced, but outside the reach of application processing and lookups. This problem may be resolved by multiple methods, for example by storing the records in a logically or physically separate data structure. This separate data structure would typically be a database with a data dictionary that is similar to the primary repository's data dictionary. To prevent application code from considering the out-of-deployment records in standard application operations, those records would not be included in standard application indexes.

A dynamic database is a database which is expected to change frequently throughout the course of a typical day. This is contrasted with a static database, which is a typically-static collection of data; static databases are most often used for lookup and reference purposes. Dynamic database records are records that are dynamic and created as a part of the workflow of applications. Examples of these include orders, claims and episodes. The dynamic database records may be resolved using one of several techniques, including: direct ID match and Master Dynamic Database Index (MDI) table.

The direct ID match technique creates and assigns a unique record ID to a record when the dynamic database record is created at a deployment. This ID is unique across all deployments in the Community. One way to generate these unique IDs is to prefix the sequence ID with a two digit deployment number. For example, order records in "Deployment 00" all begin with "00" such as 0011, 0012, 0013, 00155, and so on.

Thus, during synchronization of a patient record that contains a dynamic record referencing a dynamic database record with a community-wide unique ID, the dynamic database record is created at the other deployment using the same record ID and the reference is easily resolved with a direct ID match.

If using MDI table technique, no special treatment is done at the time of creation of the dynamic database record at the original deployment. During synchronization of a patient record, the receiver deployment may create a new record corresponding to the incoming dynamic database record and then assign it a local ID, storing the original ID that came with the record in an MDI table with the deployment information for ease of matching records during later synchronization. This table is sent along with the dynamic database record whenever a message includes that record's information.

Both techniques require on-the-fly record creation at the time of patient record synchronization. For this reason, the patient record synchronization messages contain all necessary information to create the dynamic database records. Like the patient record, dynamic database records will also be divided into groups and leaf groups to easily form a portion of message containing the record information.

Since the dynamic database records are linked into a patient record, the edits made to these records are propagated up into the patient record and the generations are updated. These records themselves also have generations assigned to them and the groups inside the record also have generations. This is helpful at the time of updates triggering to determine the exact data set which has changed.

The direct ID matching technique minimizes the processing needed to point the patient fields to the new record IDs. To accomplish this, the participating deployments should be tightly affiliated with each other and use the same algorithm to generate community wide unique IDs for the records. Loosely affiliated deployments are unlikely to be able to define the rules required by direct ID matching. MDI table mapping should be used to resolve patient record pointers instead.

The type of technique used for various dynamic database records at a deployment is configurable in the community global setting. At the time of filing incoming messages for patient record synchronization, the settings are referenced for resolving the data pointers correctly. The settings chosen will depend on the affiliation level of participating deployments.

Selection lists for data elements in a database record are either a standard part of the system or defined by the deployment. If a selection list is a standard part of the system, then the data element pointing to the selection list will be resolved using direct ID matching. If a selection list is partly system-standard, then the part of the selection list which is standard will be resolved using direct ID matching. For selection lists that are defined in full or in part by the deployments, there may be at least three techniques available to resolve them. The types of mapping technique to be used for various selection values on a deployment are configurable in the community global setting. At the time of filing incoming messages for patient record synchronization, the settings are referenced for resolving the data pointers correctly. These techniques include, for example: direct ID matching, Community ID, and Master Category Index (MCI) table. A community ID is an identifier that is unique across the community of participating deployments. A Master Category Index is a community-wide index of selection lists.

Direct ID matching uses the IDs of the selections in the list itself to resolve a pointer in a patient synchronization message. This technique requires that the same ID be used for each selection list based data value throughout the Community.

In the Community ID technique, the sending deployment may convert the selection list ID into a Community ID in the synchronization message. The receiving deployment, when reading the message, may convert the Community ID to the local ID for that selection list value. Each deployment stores the Community ID for each selection list value in each list on their server.

In the MCI table technique, the sender deployment sends the local selection list ID for the field in the synchronization message and the receiver converts the selection list ID to a local ID using a master selection list ID index mapping table where the local selection list ID is mapped to IDs for the same selection list value on other deployments. Each deployment stores the MCI table for each selection list value in each list on their server.

The direct ID matching and the Community ID techniques are the recommended techniques because they do not require the extra processing needed for mapping IDs locally. These are the techniques that should be used for a tightly affiliated Community.

In all the techniques discussed above, the selection lists must be present at a deployment for the correct resolution of that data pointer. The EMFI can be used to assign Community IDs to selection list values and also for allowing selection list management. In this case, the EMFI can be used to publish selection list value changes to the Community, too. A deployment can have rules set up to deactivate certain selection list entries in a list received from other deployments. If the Community is not using the EMFI, then the selection lists may be periodically imported from the Community into each deployment.

The settings are dependent on the affiliation levels across the deployments when building the selection lists. If using the direct ID matching technique, then selection list IDs and values are created by the owner deployment and published to all deployments, cannot be changed, and all deployment must have the same selection lists, IDs, and values.

If not using the direct ID matching technique for a selection list, a deployment can assign its own selection list ID and value because the CID is assigned and used to resolve the data pointers. The selection list, selection list values, IDs, and CID are published to the participating deployments, which can then assign their own local ID to the selection list values, or change the values as needed.

Another data mapping issue to be addressed is the correspondence of patient events between deployments. An event is represented in the patient database through an Event Serial Number (ESN) and an Event Date. An event's ESN is unique within a system (deployment) for that patient record. The mechanism of generating a community wide unique ESN is similar to the ID generation technique for dynamic database records.

During patient record synchronization, all the patient's events are represented in the message content along with the rest of the patient record data. As a patient can have multiple events on a given date, synchronization of events between deployments is a challenge, as two deployments can create events for the same date and can potentially overwrite each other's events during record synchronization.

To resolve events within the patient record across deployments, a Unique Event Identifier (UEI) is assigned to each event in all patient records. The UEI for any patient event is unique across all deployments in the community.

When synchronizing a patient record from one deployment to another, an event is represented in the message using the UEI. The receiving deployment may create a copy of the event for the event date, if an event for the patient with that UEI does not exist on that deployment, assigning it a local ESN. Subsequent synchronization of the patient record with pointers to that event is resolved using the contact's UEI.

When synchronizing data elements that contain time information, the data is converted to GMT (Greenwich Mean Time) in the outgoing message and can be converted to the local time by the recipient. For data elements that store an instant (date and time combined), the time portion is converted to local time. Some data elements in the patient record are related to each other with respect to time. For example, one data element may contain a date and another a time, which collectively define an event in the patient record. Special processing in filing of these related data elements will convert the date to the correct date.

Patient Record Updates

Once a patient record or portion thereof has been copied to a remote deployment, both the remote and home deployments participate in keeping the patient record synchronized across deployments in the Community via notifications/publications until the remote deployment is finished accessing the patient record and deactivates the subscription for the patient record or portion thereof. When a patient is accessed at a remote deployment, the remote deployment is automatically subscribed to receive any updates made to the patient record or portion thereof at any other deployment via the notification broker 44.

For example, when remote deployment 22 makes a change to the patient record, it sends an Update Record message to the home deployment 20, which will in turn publish it to any other subscribed deployments 24 in the Community via the notification broker 44. Likewise, if either the home deployment 20 or another deployment 24 makes a change to the patient record while it is being accessed at the remote deployment 22, that update will be sent to the home deployment 20, published to the notification broker 44, and received by the deployment 22.

Updates sent out to the Community will only contain the parts of the patient record that have changed. This reduces the potential for conflicts and conserves system resources. The frequency and timing of updates will be controlled in part by update triggers placed at logical points in the patient care workflow.

During active patient care, the remote deployment 22 remains subscribed to the patient record and continues to send Update Record messages to the home deployment 20. Active patient care includes activity on the patient medical record, scheduling, billing processes, etc. The home deployment continues to publish updates as long as there are remote deployments subscribed.

Updating patient records across deployments can be broken into five main topics: capturing changes to the patient record, triggering updates at logical points, sending updates, receiving updates, and starting and stopping subscriptions. The system 10 design maximizes the efficiency of sharing patient data by being able to identify and send only those portions of the patient record that have changed. Thus, instead of sending the entire patient record every time a deployment requests synchronization, only the updated data groups are sent. The only exception, of course, is that the first time a remote deployment requests a patient record, the entire record must be sent.

Triggers are incidents of data modification that cause data updates to be sent to the Community. When a trigger occurs, the system identifies what, if anything, has changed in the patient record, modifies generations and the update history as needed, and populates an update queue, causing an update to be sent, as long as there are subscribed deployments for the record. Triggers may be located within application workflows or in other locations modifying the database.

For certain actions, it is desirable to share changes right away to ensure quality patient care, such as when a patient's allergies are changed. For other actions, like updating a patient's demographics, there is less immediacy, though the changes should be sent soon. The update queue is monitored by the update daemon, a process running under the operating system to handle periodic requests, which is ultimately responsible for sending the updates back to the home deployment 20, or straight to the notification broker 44 if the changes originated at the home deployment 20. The update process packages up the modified data groups in the patient record and sends them out as an Update Record message.

Another daemon is responsible for receiving updates from the Community. This daemon validates the update message, checks for sequential continuity (as described in the Conflict Resolution section below), and then files the data. If the patient record is being updated by a local user when the message arrives for that patient, the local user's activities are not interrupted by the daemon.

For triggers to fire, the system must track changes to any data elements that will be shared within the Community. For the purposes of patient record synchronization, it is only important to know that a data element changed; knowledge of the previous value is unnecessary.

Before sending an update to the Community, data updates may be grouped and analyzed as a whole (a "batch") to optimize performance. Before sending an update to the Community, a final Pre-Transmission Action will be performed. This Pre-Transmission Action performs two actions: (1) the patient is checked to see if it should be tracked. If the record is at home and no remote participant has ever subscribed to the record, tracking will not occur. This saves the overhead of tracking groups and incrementing generations for patients who do not receive care outside of their home deployment. Once a patient receives care outside of the home deployment then tracking should occur. (2) For each data element tracked in the pending update to the Community, the Pre-Transmission Action marks the data element's group as "changed." If an update occurs in a non-patient database which is related to the patient database, a special index is updated to reflect the change. The index contains a reference to the patient record, a reference to the related database, and the record id in the related database. For example, patients are linked to order records. Changes to an order record marks the order as changed and also marks the special index with a reference to the patient, the order, and the database in question (in this case, the Orders database).

Figure 15:
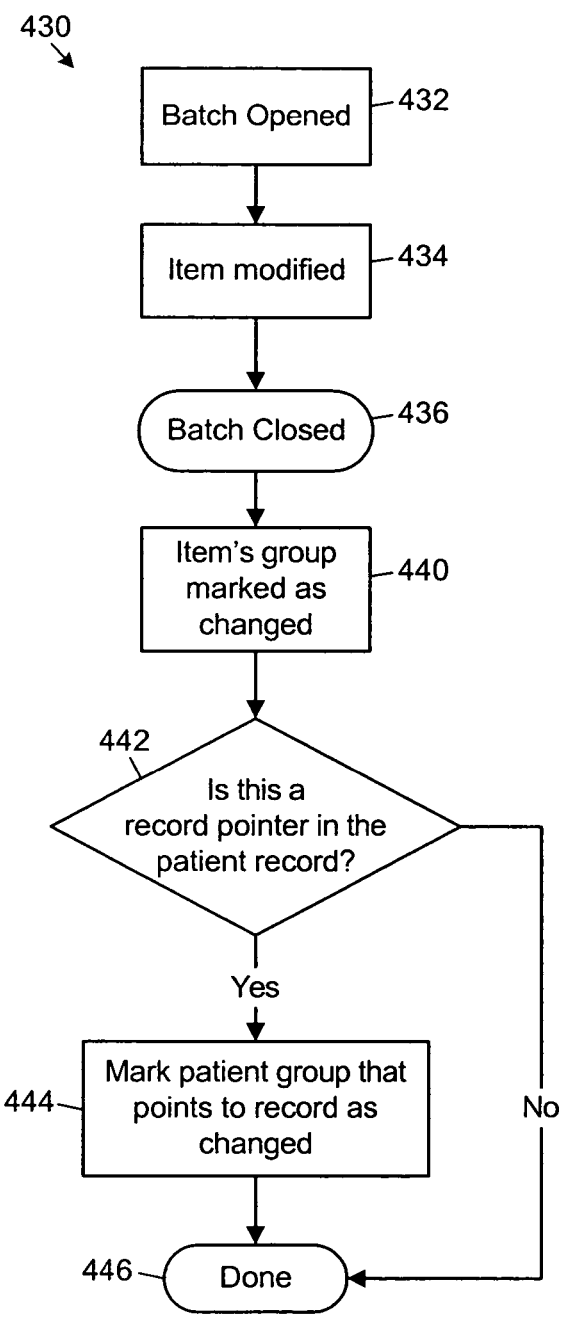
FIG. 15 is an exemplary flowchart representation of a routine that may be used in tracking patient level changes.

FIG. 15 is an exemplary flowchart of a routine 430 illustrating several steps used in tracking patient level changes. A batch is first opened (block 432), a data element is modified (block 434), and the batch is closed (block 436). The routine 430 then causes the data element's group to be marked as changed (block 440). If it is determined at the block 442 that it is a record pointer in the patient record, the patient group that points to the record is marked as changed (block 444), and the routine ends (block 446).

Figure 16:
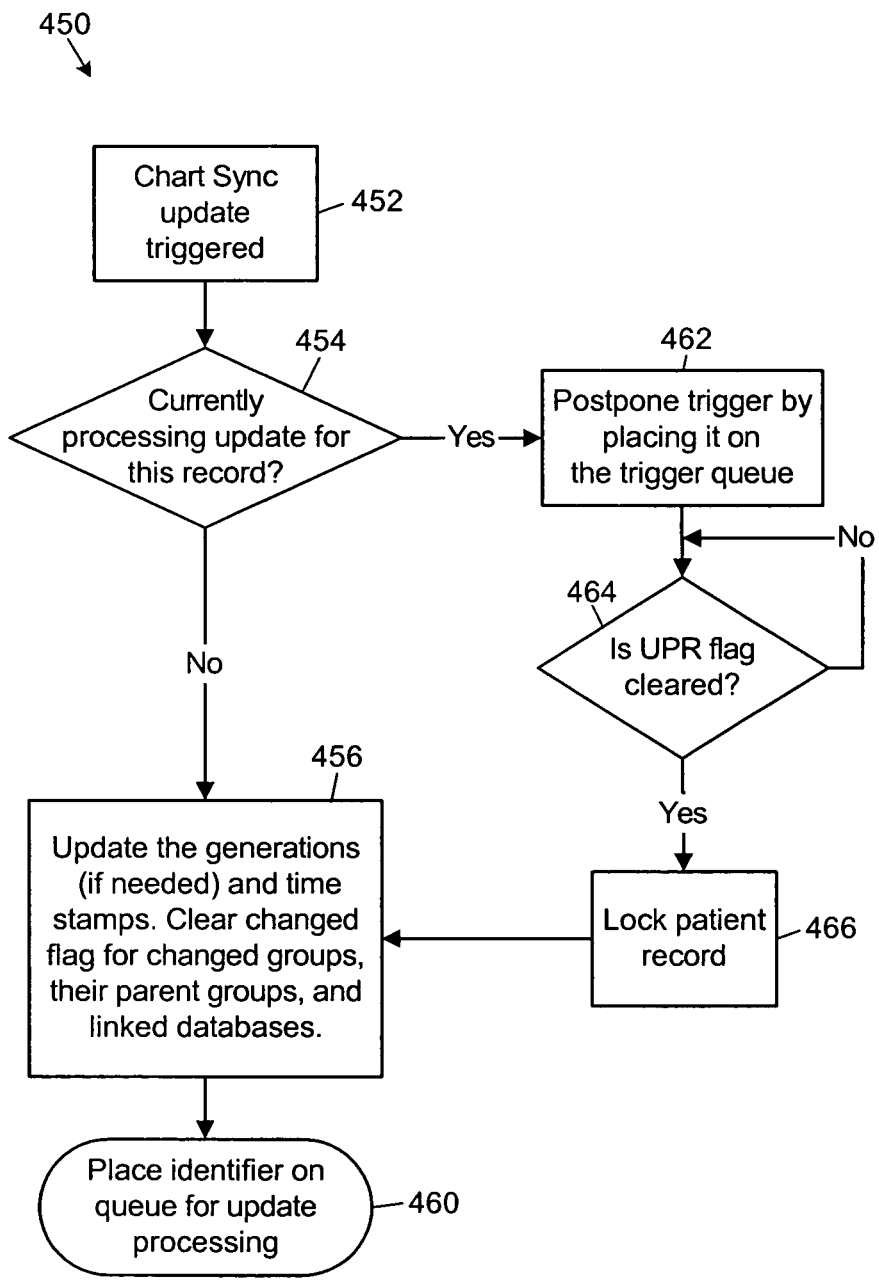
FIG. 16 is an exemplary flowchart representation of a routine used in a triggering queue.

FIG. 16 is an exemplary flowchart of a routine 450 illustrating several steps used in a triggering queue. Logical points within application workflows trigger a patient record update to be sent to the Community (block 452). These trigger points are functionally separate from the actual tracking of changes to the patient record by the Pre-Transmission Action. The two functions serve different purposes: Tracking is required to determine which data elements are new or changed; update triggers are logical places to transmit data. Three examples of potential trigger locations in application workflows are: when a patient's allergies are updated, when orders are signed, and when results come into the system through an EDI interface.

A trigger, as the name suggests, triggers the update method. The trigger indicates to the record synchronization processes the intention of a deployment to send out an update for a patient record or portion thereof. If no other deployment in the community is subscribed to receive the patient record updates, then the update will not be sent.

The trigger updates the generations, the update history, and timestamps for the record's group structure and then places the ID of the record on the update queue (block 452). The update queue is processed by the update daemon. This daemon can operate on either the production server 30 or shadow server 32. The latter is preferred for efficiency reasons, since it doesn't consume resources on the production server 30 and thus minimizes its effect on local users. The update daemon may be moved to the production server 30 as necessary, for infrastructural reasons.

When a trigger is fired, the daemon performs several functions. It first checks the UPR flag (block 454). This flag indicates that an update is currently being processed for a record. If the update daemon is currently processing the same record, the trigger will be postponed. A background daemon on the production server 30 will fire postponed triggers and is explained below. Since the trigger is postponed, the process does not wait for the UPR flag to be cleared. The process, in effect, skips over the trigger and continues executing. Local user interaction is allowed to continue with minimal delay.

If it is determined at the block 454 that the UPR flag is not set, then for every group marked as changed the following is done: the group is time stamped with the current time; the current generation of the group is copied to its update history table; the generation of the group is incremented to 1 plus the LGP; the changed flag is cleared; and the group's parents is traversed up to the top level record node. Each parent group has its time stamp updated and its generation incremented if necessary. The trigger finds the linked databases that have changed through the special index described above and updates the time stamps and the update history, increments the generations, and clears the change flag in the same manner.

It is possible that the generation of a given group has been incremented by a previous trigger before the LGP was updated by the current trigger. This could occur if two triggers fire close in time to each other, and the second trigger fires before the UPR flag is set. If the second trigger is working on the same data group, then the generation would already be LGP plus 1 and would not be incremented again.

The software component 450 then causes an entry to be placed on the update queue (block 460). This entry is the patient identifier. If there is already an entry on the queue for that record ID, another one will not be added.

If the UPR flag is already set, the trigger is placed on a different list called the trigger queue (block 462). This queue exists on the production server 30 because the update daemon needs to lock the record (block 466) and update the groups' generations, time stamps and changed flags (block 456).

After waiting for the UPR flag to be cleared for the given record (block 464), the trigger queue carries out the same set of steps listed above: updating the current generations, the update history, and timestamps for each changed data group, their parents and linked supporting databases (block 456), and finally putting the entry on the update queue (block 460).

It should be noted that the information collected by multiple triggers may be sent out as one update. This may happen due to the timing of the shadow server processing or due to postponing triggers, such as when triggers are allowed to collect for a specified period of time before the update is sent, as may be configured to occur in hospital scenarios.

Figure 17:
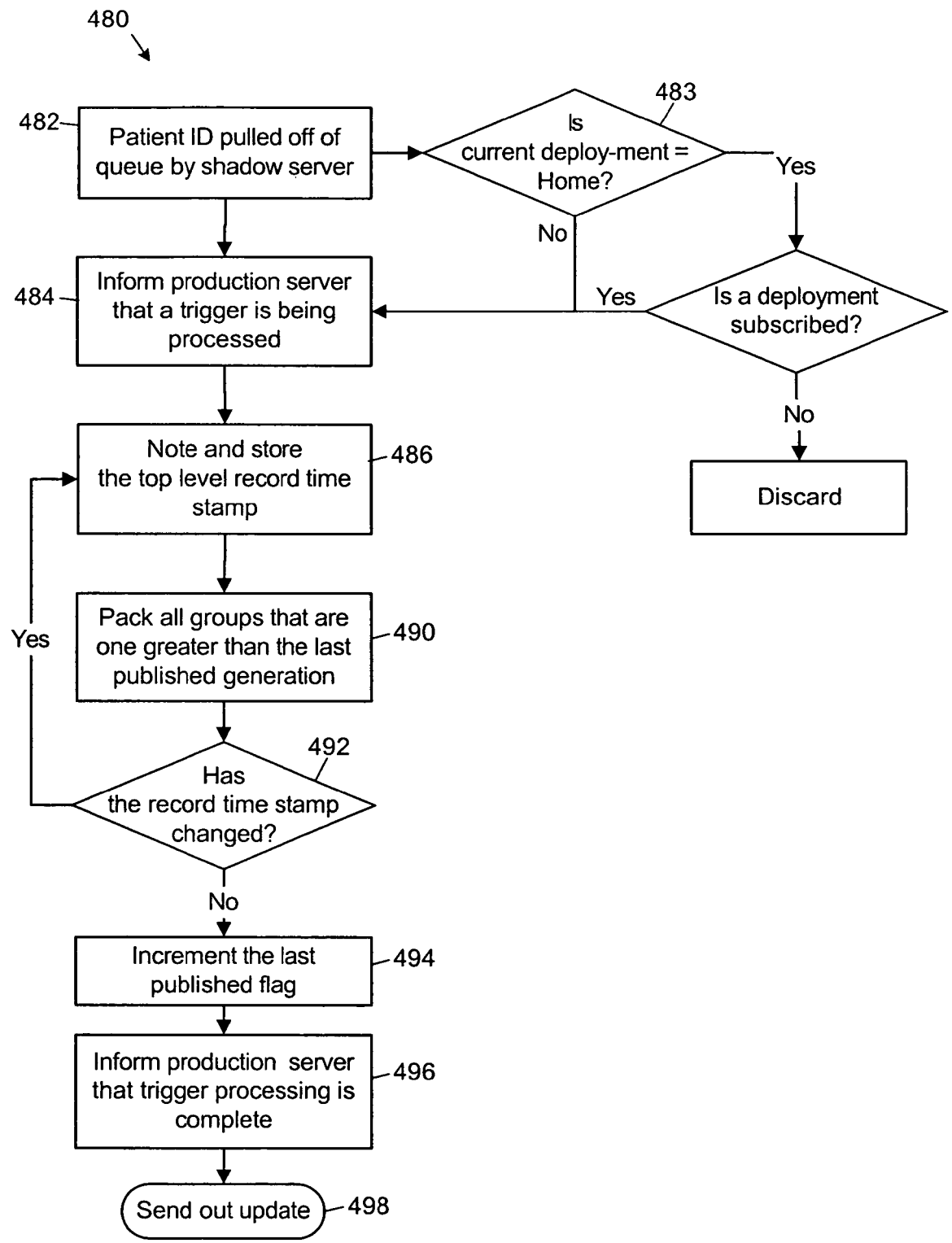
FIG. 17 is an exemplary flowchart representation of a routine used in the processing and sending of updates to a record.

FIG. 17 is an exemplary flowchart of a software component 480 illustrating several steps used in the processing and sending of updates to a record. The job of the update daemon is to send out updates made to the patient record at the local deployment. Changes made at remote deployments 22 and 24 are always sent to the home deployment 20 for processing and evaluation first. The home deployment 20 publishes the changes directly to the notification broker 44 for distribution to subscribed deployments. The update daemon waits for entries to appear in the update queue. When an entry is detected, it is pulled from the queue and processed. The daemon traverses the record's data groups looking for any groups whose generation is one greater than the last generation published.

A last generation published (LGP) flag attached to each data group is used by the update daemon to determine if a group's generation is one greater than the last generation published. Meanwhile, a UPR flag attached to each data group serves to prevent triggers from making changes to the data group while the update daemon is packing the information.

Both flags should be set on the production server 30 and are controlled by the update daemon. In instances where the update daemon is operating on the shadow server 32, there may be another queue that takes requests and executes them on the production server 30. The system 10 is designed to take into account the delay introduced by this queue.

Still referring to FIG. 17, the daemon 480 causes the record ID to be pulled off the update queue (block 482). The daemon 480 checks to see if an update should be sent out for this record (block 483). If the record is a home record, then it checks to see if anyone is subscribed and if so, proceeds with sending the update. If the record where the change occurred is a remote record, the update is sent out.

The daemon 480 then sets the UPR flag. The UPR flag is set on the production server 30 (block 484). If the daemon is located on the shadow server 32, then triggers can still fire from the time the daemon initiates this action until the flag actually gets set on the production server 30. Because the LGP has not been incremented yet, triggers may still increment generations to the same level (LGP+1) as the modified groups currently being processed on the shadow server 32. Once the UPR flag is set, triggers are postponed until the flag is cleared. Therefore, the daemon will never see a higher generation than LGP+1.

The daemon 480 then notes and stores the time stamp from the top-level data group into some form of local storage, for example, a variable in RAM (block 486). This information is used to see if the top-level time stamp has changed from the start of the tree traversal to the end (i.e. something has updated the patient record while the patient record was being traversed).

The group structure is then traversed, packing all the groups that have a generation of one higher than the LGP into the message being sent out (block 490). The message contains the data, the generation, the update history, and the time stamp for each group.

When the update daemon 480 finishes traversing the data groups, the time stamp of the top-level group is compared to the saved time stamp (block 492). If the top-level group's time stamp has changed, it means that a trigger fired for that patient since the time the daemon began processing the queue. The update daemon then searches the group structure again for any newly-changed groups (LGP+1) and repacks the message. This allows the capture of additional triggers that have fired since the tree traversal was started. Groups that haven not changed are not repacked.

The daemon 480 continues to loop through the data groups until the top level time stamp and the saved time stamp do not change between traversals. This explains why it is important that the shadow server 32 not fall too far behind the production server 30, lest a trigger fire but its time stamp update not appear in time for the update daemon to notice. This situation can be avoided by having the update daemon 480 wait for a given period of time before the time stamps are compared.

The daemon 480 will then cause the LGP flag to be incremented for the given record. The LGP flag is incremented on the production server 30 as well (block 494). The UPR flag is then cleared in the same manner, thereby signaling to production that triggers may be processed again (block 496). The daemon 480 then causes the update package to be sent out to the Community (block 498). It is important to note two key points: (1) If the update is for a patient record stored on the remote deployment, the update is sent directly to the home deployment 20. The home deployment 20 is in charge of publishing the change to any interested (i.e. subscribed) parties. (2) If the update originates at the home deployment, the update will be published to the Community at this point.

Figure 18:
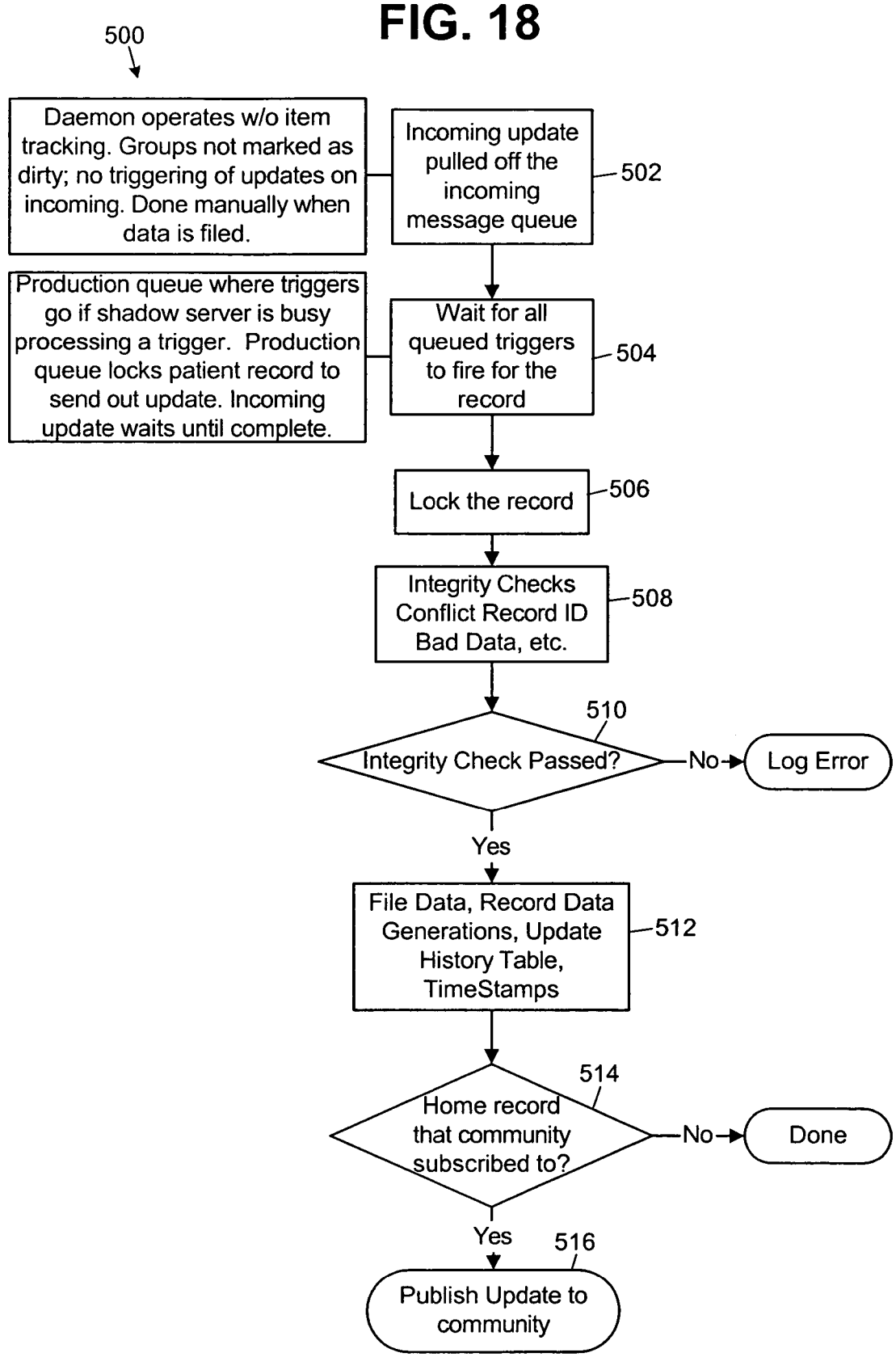
FIG. 18 is an exemplary flowchart representation of a routine used in receiving and filing data received from the community.

FIG. 18 illustrates an exemplary flowchart of a routine 500 illustrating several steps used by deployments when receiving and filing patient record updates received from the Community. Examples of where this can occur include: (1) A remote deployment is subscribed to receive updates to the patient record. (2) The home deployment may receive an updated record for a patient whether any subscription is active or not.

The processing of incoming updates may be conducted by the daemon 500 running on the production server 30. This daemon 500 may not have data change-tracking enabled since the groups, generations, and update history already have been set from the sending deployment. The groups should not be marked as changed when they are filed as that will cause triggers to update the generations and have the shadow server send out an update, causing unnecessary work and an unnecessary loop.

Still referring to FIG. 18, the messaging system places an update from the Community on the incoming message queue for the daemon 500 to process. The daemon 500 pulls an update message from the incoming message queue (block 502). This could be an Update Record message or a published update. Deployments receive direct Update Record requests for records homed locally. Deployments receive updates from the publish/subscribe system when they are subscribed to patient records housed on remote deployments.

The daemon 500 waits for all processing to be done upon the record (block 504). The trigger queue is checked to see if it is waiting to fire any triggers for the patient. If the trigger queue is waiting to process triggers on the patient record, then the daemon waits to file the update until the trigger queue is finished with the patient. Then the daemon 500 acquires a lock on the patient (block 506). This is done to allow any local processing on the record to finish before applying remote updates.

The daemon 500 then performs any integrity checks on the data to be filed (block 508). Some possible errors may be receiving an update to a patient that is not homed locally and not subscribed to, badly formed data, etc. If the check fails then an error is logged locally, the sender is informed of the error and the data is not filed. The incoming data goes through conflict detection at this point. Conflict detection is making sure the data can be filed without destroying logical integrity and is discussed in the Conflict Resolution section below.

If it is determined at a block 510 that the integrity check passed, the data for the update is filed (block 512). Along with the data, the generations, update history, and timestamps are updated from the message. The daemon 500 checks if the message received needs to be published (block 514). If the update is for a record homed locally, then the daemon checks if anyone is subscribed to the record. If someone is subscribed, then the message is published to the Community (block 516). This follows the model that all updates are sent to the record's home deployment first and then published to subscribed deployments in the Community.

The patient record contains foreign keys. The patient record synchronization system supports sending updates to these linked databases. There are at least two approaches to triggering patient record updates. One is a general patient trigger and the other is a more specific trigger for supporting linked databases. The general patient trigger will need to find any updates to linked databases. The specific trigger will need to find the patient affected.

Before the two approaches to triggering are described, a reminder of how changes to linked databases are tracked is in order. The data change tracking feature tracks changes to any linked databases in the patient record. When a group of data changes is finalized, the following happens: (1) The linked database groups are marked as changed. (2) The patient record that points to the linked database is discovered. There are a few methods to discover the patient involved. For example, back-pointers from a patient referral record to all records in other databases that refer to patient referral record can be used. (3) The special index containing the patient, the linked database, and the linked database record identifier is updated.

The general patient trigger fires for updates to the patient record due to actions such as updating the patient's allergies list or ordering a medication. The trigger receives the patient record identifier and a context string saying why the trigger was fired. The trigger may not be told explicitly that a linked database was changed and needs to be sent out as part of the update. To handle this, the trigger does the following: (1) Look for any groups in the patient record marked as changed to get the patient level changes. (2) Look into the special index created upon batch close to find any linked database changes. For each linked database record found, the record's groups and generations are updated. The index is cleared. (3) The queue for the update daemon receives the patient identifier and the linked databases and linked database record identifiers. The daemon processes each record identifier to create the Update Record message.

The following example illustrates a situation where the patient record is updated and a linked database record is created. A physician orders a lab test for a patient. As a result, the patient record is changed to have one more order and an order record is created. The batch close will mark the order record as changed, the patient's orders group as changed, and mark the special index. The "orders added" trigger fires for the patient. The trigger updates the generations and the update history of the patient's order group and parents. The trigger then looks in the special index, finds the order that was added and updates its generations and groups. Then, the patient identifier and order identifier is placed on the update queue for the update daemon to pack up and send out.

A more specific trigger fires when changes to only linked databases occur. An example is adding a result to an order: Nothing in the patient record changed, only a result was added, causing the need for an update to be sent. The trigger that fires contains the linked database record identifier, not the patient identifier. The trigger is not told explicitly which patient is linked. In this case, the trigger does the following: discovers the patient involved with the change by using the above-mentioned techniques, updates the groups and generations of the linked database record, clears the special index for the linked database record, and places the patient identifier and record identifier on the update queue for the queue daemon to create a Update Record message.

The trigger needs to know the patient involved with the change so that the update can be sent as a patient record update. The patient is not searched for changed groups in this case because the trigger is specifically for the linked record.

Conflict Resolution

The system 10 allows separate deployments of software to operate independently, yet share patient records by exchanging patient record updates with each other as needed. The very nature of this system creates the possibility that more than one deployment can update the same patient record simultaneously, and that the order in which those updates actually occurred could be lost when they are returned to the home deployment. This section explains how patient data is managed by ensuring that updates are built upon one another, so that older updates do not overwrite newer updates. It also discusses how conflicting updates are handled when they occur.

During patient record synchronization, only data that has "sequential continuity" is considered safe to file. Groups of data contained within a patient record received by a deployment are compared to all existing information for that patient to determine if any of the incoming information is older than the existing information. This comparison prevents older information from overwriting newer information. If the incoming data is built upon the existing data, the data is considered to have sequential continuity and is filed. If an incoming update is older than existing data, which can happen due to the asynchronous nature of the system's delivery system, the data is not filed.

The system 10 uses the generations and update history of the data groups, described earlier, to compare incoming data with existing data and to maintain sequential continuity of the information. This description also defines the process that deployments take when they encounter data that does not have sequential continuity. All deployments check for conflicting data whenever an update to a patient record is received. Users at the home deployment 20 are responsible for resolving conflicts and pushing the merged changes back to the subscribed deployments. When deployments detect a conflict, they inform the user. Remote deployments may maintain data they file at their sites after conflict is detected and keep any of the non-conflicting data filed after the home deployment sends the corrected patient record. As an overview, conflict detection does not look at the data in the message. Only generations and the update history are used to ensure sequential continuity.

As previously mentioned, the patient record is divided into smaller groups. Each smaller group can be sent individually across deployments. This allows for different deployments to edit different parts of a record without conflict. Only when the same data group is edited on different deployments can conflict occur.

In order to detect conflict, each group has a generation associated with it. Along with the generation, the group has the update history table including each deployment that has contributed to that group and the latest generation that was contributed by that deployment. If a deployment were to increment the generation of a data group more than once, only the latest generation change will appear in the table. In that respect, the table is not a complete history, nor can it grow to an unmanageable size, regardless of the number of times a record is edited.

By default, the generation of a data group that has never left the home deployment is 1, no matter how many times the home deployment updates that data group. Once it is shared with other deployments, the generations for each changed data group is incremented when triggers are fired according to the following algorithm:

For each data group marked as changed, the following actions are taken: (1) Check to see if the generation needs to change. If the generation has already been incremented to 1+the last generation published, then the generation doesn't need to be incremented again. (2) If the generation needs to be incremented, the current generation is placed into the update history table corresponding to the deployment that contributed that generation. The current generation is then incremented and the current deployment assigned.

The following scenario illustrates this algorithm. In this scenario, the home deployment for a patient record is deployment A. Deployments B and C make updates to the patient's demographics data group.

Figure 19D:
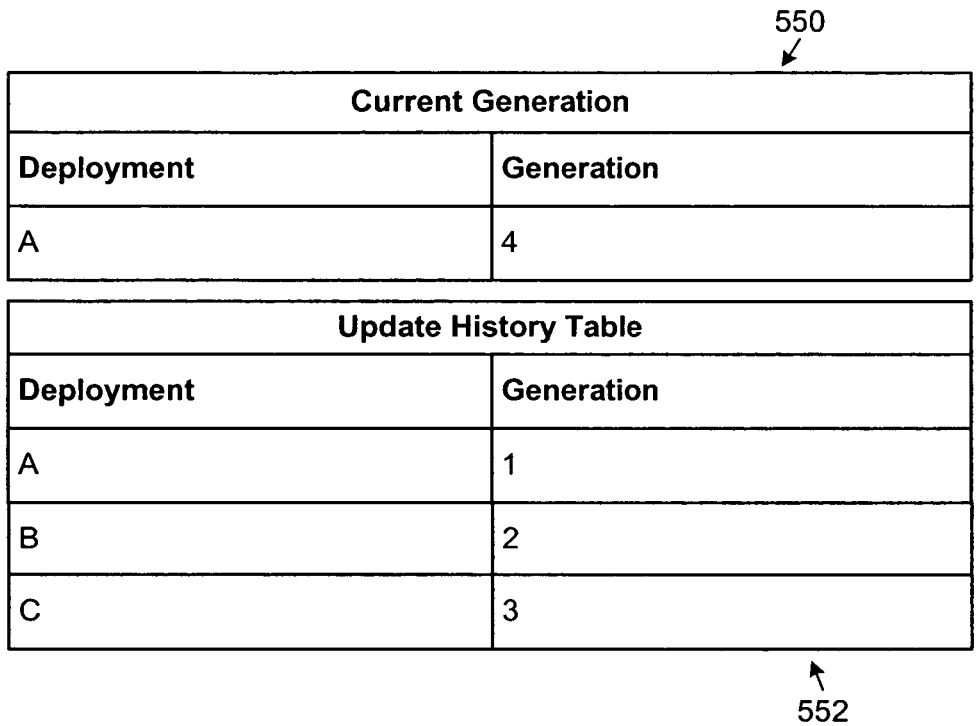

FIG. 19A illustrates an exemplary current generation 530 for deployment A for demographics. Before any other deployments request the patient record, the demographics data group is at generation 1 and there are no entries in the update history table of FIG. 19A.

When the patient arrives for care at deployment B, a Get Record message request is automatically sent to the home deployment so that staff may begin working with the patient record. When the Send Record message is received and the patient record becomes available, a staff member at deployment B updates the patient's demographics, causing the current generation of a data group to increment to 2. The update history table records that deployment A contributed generation 1.

Deployment B sends the updated demographics information back to the home deployment. There, the change is evaluated and determined to have sequential continuity, and the updated demographics group is filed. This is illustrated in the current generation 540 and update history table 542 of FIG. 19B.

Deployment C then accesses the patient record. When it receives the patient record from the home deployment, the demographics data group is at generation 2, and the information appears as deployment B last recorded it. A staff member at deployment C updates the patient's demographic information. This causes the current generation to increment to 3. This is illustrated in the current generation 546 and update history table 548 of FIG. 19C.

The update made at deployment C is sent back to the home deployment and filed. The patient's demographics are changed once again at the home deployment, deployment A. Now, the generation of the demographics data group is incremented to 4. This is illustrated in the current generation 550 and update history table 552 of FIG. 19D. The update history still shows the order of all contributions by the deployments to the demographics data group.

Figure 19E:
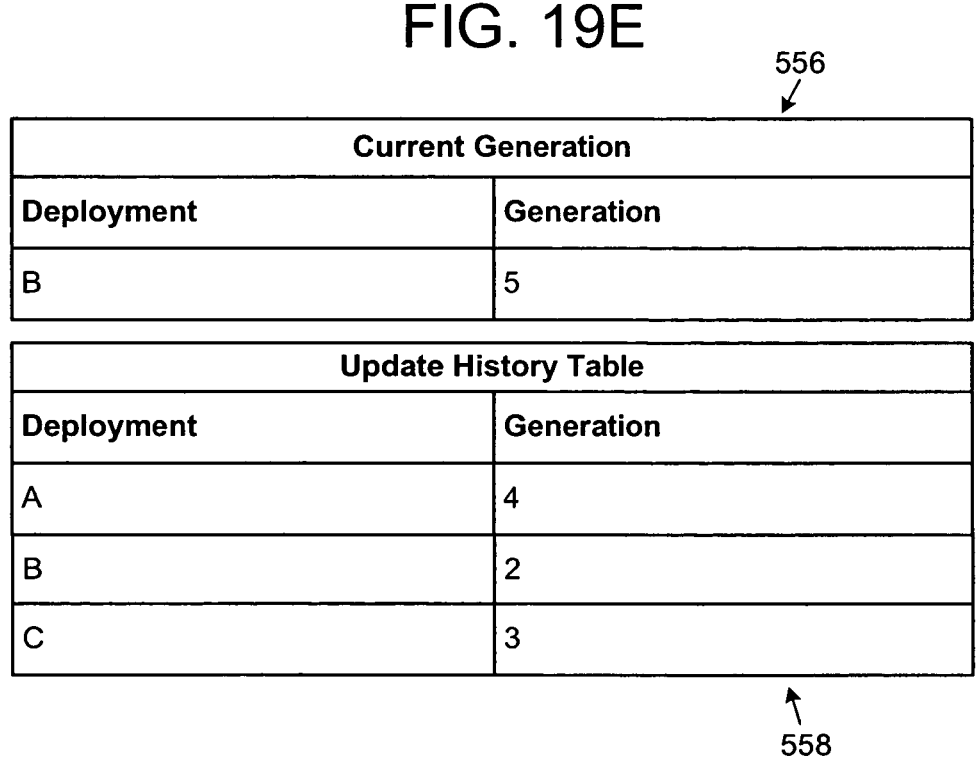

At this point, deployment A appears in the current generation 550 and also in the update history table. The same deployment will never appear in the update history table more than once; only the most recent past update is recorded The home deployment publishes this update to deployment B and C. When deployment B receives the update from the home deployment, it changes a data element in the demographics group again. This causes the current generation to increment to 5, and for deployment A's original generation information (1) to be removed from the generation table, leaving only its most recent update (4) in the update history table. This is illustrated in the current generation 556 and update history table 558 of FIG. 19E.

The fact that deployment A contributed generation 1 is no longer recorded in the update history table. Because it is assumed that each generation is built upon the last, the information about generation 1 is no longer needed. It is implicit in the logic that generation 4 from deployment A was built upon generation 1 from the same deployment. This is illustrated in more detail below.

It should be noted that each changed data group within a patient record is considered and compared separately. Only the groups that have sequential continuity are filed. Those that are in conflict are not filed.

Conflict detection is done whenever updates are received. It doesn't matter if the record is a remote or local record—every record coming into any deployment, whether solicited or via broadcast, needs to be checked for conflict. The actions a deployment takes when it encounters conflict depend upon whether the deployment is the home deployment for the record or not. Those actions are described below.

To decide whether or not an incoming piece of data should be filed, the deployment has to decide if the incoming data is sequentially continuous with the data stored locally. If the incoming data was built upon what is stored, then it can be filed. If not, then one of two things may have happened: (1) The incoming data may be an older version of what was filed. In that case, the filed data was built upon what was incoming (that is, the updates occurred out of order). The deployment detects this and ignores the older data. (2) The second possibility is that the incoming data did not build upon the filed data and, vice versa, the filed data did not build upon the incoming data. In this case, the incoming group has data the filed group doesn't know about and the filed group has data the incoming group doesn't know about.

The algorithm to assess and accept incoming updates includes the following steps. Each step is discussed in more detail below.

1. Check for duplicate update. If duplicate, update is ignored and no more checks are done.

2. Check if incoming update was built upon filed data. If it is then file incoming update and no more checks are done.

3. Check if filed data was built upon incoming update. If it is, then ignore (it's an out-of-order update) and no more checks are done.

If all three checks fail, then the incoming update conflicts with the filed data and it is moved to a queue for manual processing.

FIG. 19F illustrates two generations 560 and 562 where the current generations of both the filed data and the incoming data are the same. In this case, the update is a duplicate of what is filed and the update is ignored.

It is also important to check to see if the incoming group was built upon data that is filed locally. This is done by checking to see if the current generation of the locally filed group is recorded within the incoming group's update history. For example, suppose a patient record at a deployment has a data group whose current generation is at 2, due to a change that deployment B made. This is illustrated in the current generation 570 and update history table 572 of FIG. 19G. As illustrated in the current generation 574 and update history table 576 of FIG. 19G, an update from deployment C, at generation 3, is received. As long as the incoming update's update history table contains a record of deployment B's generation 2 update, the group is considered to have sequential continuity and be safe to file.

For another example, assume that deployment B unsubscribes at the point when it files the data group from deployment C at generation 3. This is illustrated in the current generation 580 and update history table 582 of FIG. 19H.

While deployment B is unsubscribed, deployment C updates the data group to generation 4 and then deployment A updates the data group to generation 5. Deployment B then accesses the patient record again. The generation and update history it receives from the home deployment is illustrated in the current generation 586 and update history table 588 of FIG. 19I.

In this example, when deployment B receives the patient record from the home deployment, the demographics data group is deployment A's generation 5, and deployment C's generation 3 has already been cleared from the update history table. This is acceptable because the incoming update history table has generation 4 from deployment C recorded. It is assumed that any new generations from a deployment in the update history table were built upon all older generations from the same deployment.

If the second check fails, then the deployment checks to see if its filed data is newer than the incoming data. So instead of checking to see if it is "behind," it checks to see if it's "ahead." To do this, the deployment examines the update history of its own filed data to see if it contains the current generation of the incoming data. If it does, then the incoming data can be ignored, since it is then assumed that the filed data was built upon the data contained in the incoming message. Thus, the same assumption that any new generations from a deployment in the update history table were built upon all older generations from the same deployment, applies here.

Figure 19J:
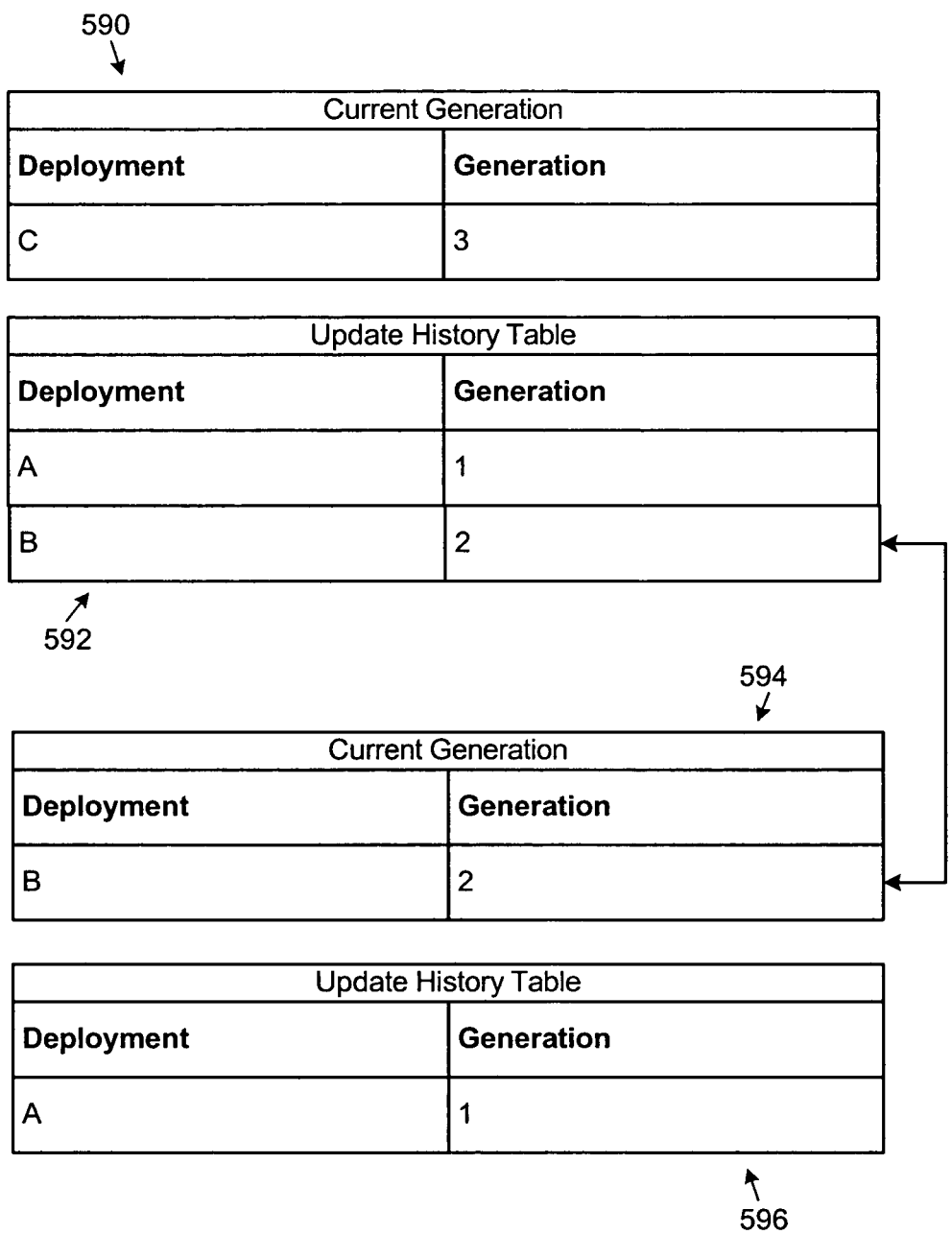

To illustrate this, consider the previous example, in which the deployment was working with the data group at generation 3 by deployment C. This is illustrated again in the current generation 590 and the update history table 592 of FIG. 19J. At this point, the home deployment sends an update that contains deployment B's generation 2. This is illustrated in the current generation 594 and the update history table 596 of FIG. 19J. This data is safe for the deployment to ignore because its existing filed data already includes generation 2 from deployment B in the update history.

If all three of the checks fail, then there is conflict between the incoming data and the data that is filed at the deployment. This could mean that any of the following are true: that the filed data group does not contain data in the incoming data group, that the filed data group contains data that the incoming data group does not, that the filed data group was not built upon the incoming data group, or that the incoming data group was not built upon the filed data group.

Figure 19K:
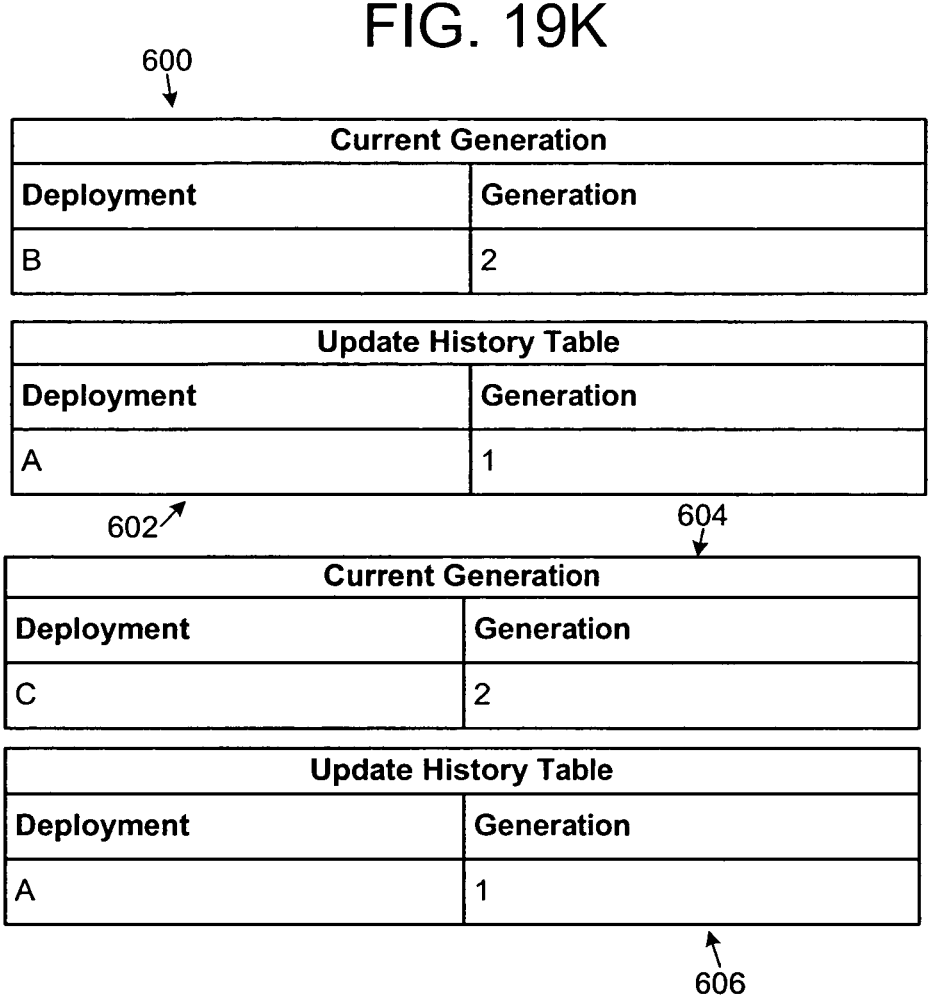

The next example illustrates an incoming update with in the current generation 604 and the update history table 606 of FIG. 19K that conflicts with the filed update in the current generation 600 and the update history table 602 of FIG. 19K.

Both deployment B and deployment C sent a generation 2 update to the home deployment without knowing about the other deployment's actions. The checks from above would fail, signaling conflict detection.

Conflict detection should be done on all incoming data, except when a patient record is pulled to the deployment for the very first time. Examples of instances in which the algorithm will be applied include when a Send Record message is received and when an Update Record message is received.

Once conflict is detected, it may be resolved so that every subscribed deployment has a consistent record for the patient. This section describes what happens at the home deployment and at the remote deployment after conflict is detected. Three independent conflict resolution techniques are described below, in order of increasing complexity. Each stage includes a series of steps used to resolve conflict.

Because all remote deployments send their updates to the home deployment for evaluation, conflict only occurs between a remote deployment and the home deployment. Thus it is assumed that conflict between two remote deployments will never occur. When conflict is detected, the home deployment does not publish the update to the notification broker for distribution to subscribed deployments until the conflict is resolved.

The simplest option for conflict resolution calls for manual intervention. The process works as follows:

Home deployment's actions: (1) Home deployment detects an update from the remote deployment that is in conflict. (2) Home deployment logs a conflict detection event. The information in the event log contains what message was sent, from which deployment, and the data in the incoming message. (3) To resolve the conflict, a user reviews the event log and makes changes to the patient record to resolve the conflict. For example, this may mean adding an allergy to an allergy list or contacting the conflicting deployment to work out the details. The only special tool used in this situation is the event log viewer to view conflicts. (4) Once the user has entered the data to resolve the conflict, the data is sent out as another update.

Remote deployment's actions: (1) Remote deployment receives an update that is in conflict. (2) Remote deployment logs a conflict detection event but files the home deployment's information anyway. Remote deployment is filing an update that is not built upon data filed with the understanding that the home deployment will send an update later that resolves the conflict and merges the home deployment's and remote deployment's data.

To summarize, the conflicts are detected but no special action is taken other than to log an error. A user monitors the error log and manually adjusts the data that is conflicting in order to resolve the conflicts.

A second, more complex option allows the remote deployment to keep its filed data until the conflict is resolved. Now deployments are informed of conflict and informed when conflict is resolved. Two new messages are introduced here: (1) A record conflict notification message. (2) A conflict resolution message.

A tool to resolve the conflict sends out the conflict resolution messages. The process works as follows:

Home deployment's actions: (1) Detect the conflict and do not file. Log the conflict detection event on the conflict work queue. (2) Publish a conflict notification message to everyone subscribed to the patient. (a) The message contains the conflicting information in a user-friendly format. (b) The deployments receive this information and store it in the database linked to the patient record as a conflicting data message. (c) The user interface alerts end users when conflicting data messages exist. (d) The user has the option to view the conflict information in an easy-to-read format; for example, an HTML report. (e) Security to view the information is respected. Users need the proper security to view the information contained in the conflicting data message. (f) The end user can then take into account the conflicting data when making medical decisions. (3) A user is responsible for going through the conflict work queue and resolving the conflict. The work queue is part of a tool for conflict resolution. The tool shows the conflicting messages and allows the user to take certain actions such as merging data, deleting data, and inserting data. The messages may be transformed from their XML base to a more readable for the end user. (4) Once the user is finished resolving the conflict, the conflict resolution message containing the updated record is sent to all subscribed deployments.

This conflict resolution message is different than a normal update message for two reasons. The first reason is that the conflicting deployments' update history is incorporated into the update history to inform the Community that the message was built from two sources. For example, given the conflicting generations illustrated in FIG. 19K, the merged group is illustrated in FIG. 19L.

Figure 19L:
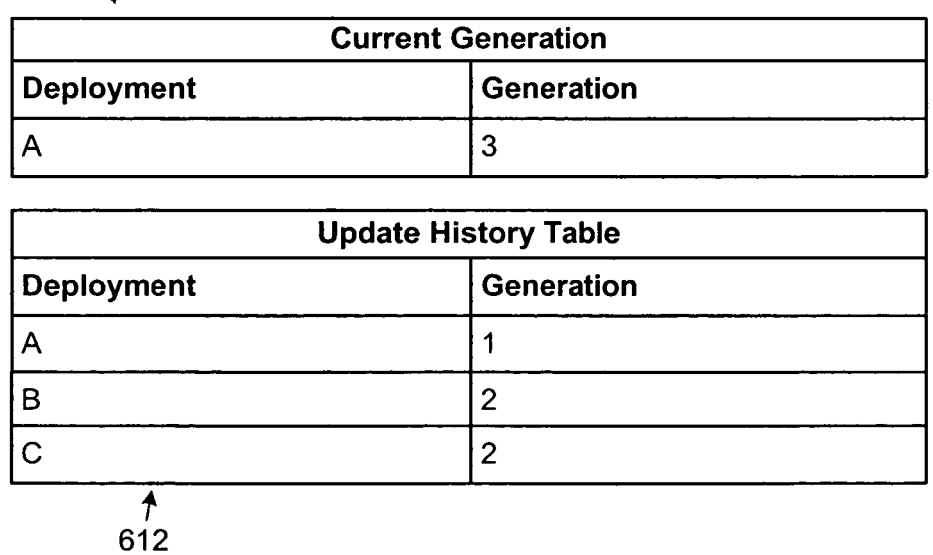

FIG. 19L illustrates how the generation 610 and update history 612 would look for the group once the conflict is resolved. Both generations from the conflicting groups are recorded in the update history table and the home deployment increments the generation to send out to all subscribers. Note that, given the rules above for detecting conflict, both conflicting deployments would accept this update because it was built upon their latest generation.

The second reason is that another flag in the message specifies that a conflict was resolved. Remote deployments may use this flag to indicate that the conflict no longer exists within the patient data.

Remote deployment's actions:

(1) The remote deployment detects conflict from the home deployment and does not file but stores the message in a separate data cache. The remote deployment keeps the data it generated locally and stays consistent locally until the conflict resolution message comes. (2) The remote deployment informs the end user of the conflict and allows the end user to view the conflicting data. This information may be medically relevant for patient care and should be available to view. This data is not discrete but a user-friendly HTML report. (3) The remote deployment will file the conflict resolution message data when it arrives. (4) The remote deployment will erase the conflict detection message informing the end user of conflict.

It is possible that some conflicts will be able to be resolved without manual intervention. For example, if two deployments add to a data table such as an allergies list, the list could be merged automatically.

A final option, most complex, uses programmatic logic to resolve conflicts. The logic is specified at the data group level. For example, code may be set up to resolve allergy conflicts. The logic executes and returns a value indicating success. If successful, the conflict resolution message is sent out and the work queue is not updated. If not successful, manual conflict resolution (described in the second option above) is invoked (work queue updated, conflict detection message, conflict resolution message).

It is possible that a remote deployment in conflict may continue to receive updates to the group that is in conflict. In such a case, the remote deployment continues to reject (not file the data) and directs the message instead to the view-only cache of the conflicting data (assuming the second option).

If the remote updates the conflicting group, it still sends to the home deployment. The home deployment detects the conflict and adds the data to the existing work queue entry to be resolved at one time. It is also possible that a remote deployment in conflict sends an update to the home deployment at the same time the home deployment is sending the conflict resolution message. If this occurs, the remote deployment rejects the conflict resolution message and makes no change to its data. The home deployment generates a new entry on the conflict resolution work queue. The conflict will be between the proposed resolved record and the remote deployment's new update.

Exception Management

During the normal flow of patient synchronization messages, exceptions can occur, for example when patient record requests are sent to the wrong deployment, messages are formatted incorrectly, or messages contain conflicting patient information. These exceptions to normal functioning are organized by type and logged in a centralized database at each deployment. The information stored for each error occurring during the synchronization process differs per error type. Users may be provided with a central location to view all logged exceptions on a deployment and the patient synchronization messages that caused them. Resolution of these conflicts is done by the patient's home deployment.

It should be noted that errors that occur in the system 10 are processed and logged through a common error handling service. The detection of record synchronization errors may occur on the database server during the record synchronization message processing. Any error occurring during the patient record synchronization process may be logged on the database server of the deployment where the error is detected. This database may also store the errors sent to the deployment from other deployments.

Exceptions are recorded in a database. Any message used during patient record synchronization can cause an exception to be logged. These messages include, for example, Find Patient, Get Home, Get Summary, Get Record, and Update Record. The exceptions logged in the database are made available in display-only format by a standard reporting utility. Once an exception is logged in the database, it may be necessary to take further action manually. For example, a message may need to be sent to the deployment that caused the exception to be generated.

Only users with the proper security permission are allowed to view the patient synchronization messages that caused the exceptions to be logged.

Each exception type signifies a unique condition requiring a different set of actions to resolve the condition. Some exception types specify errors that may require attention. Others indicate that one deployment caused an exception to be logged on another deployment.

Various errors can occur during the patient record retrieval process. Some errors that can occur during the record pull process include: (1) infrastructure errors, (2) functional errors, and (3) data formatting errors. Examples of infrastructure errors include: being unable to contact the EMPI for retrieving the value of patient's home deployment, being unable to contact the patient's home deployment to retrieve summary information for the patient record, a subscription request failed, and a Get Summary request failed.

Two examples of functional errors include 1) an error about the patient's home deployment is returned and 2) in response to a Get Summary and Get Record message, a deployment may raise an error saying that it is not the home deployment for the patient record. The latter is likely if a patient record pull is requested during the process of re-homing the patient. (Re-homing is the process of moving the home of a patient from one deployment to another.) If this error occurs then the remote deployment is notified of the wrong home error and the remote deployment needs to request the patient record pull from the correct home.

Two examples of data formatting errors include 1) Send Record message being incomplete (didn't receive all the data for a patient record in response to the Get Record message) and data mapping errors (cannot resolve data pointers as per the local deployment rules for techniques to resolve them, such as for static master file records, selection list values, dynamic database records, or events in patient record.)

The exception types described below serve as examples of typical exceptions that may be encountered. As the precise exceptions may vary without departing from the scope of the invention, the following examples are not meant to serve as a comprehensive list of exceptions the system may be capable of handling.

One exception type, Wrong Home, indicates that a patient synchronization message was sent to a deployment that is not the home deployment of the patient specified in the message. This may occur while a patient is being re-homed and the Community is not yet aware of the new home deployment. When a Wrong Home exception is generated, a message is sent to the requesting deployment telling it to log a Remote Exception Notification exception so that staff there will know that it caused a Wrong Home Exception at the current deployment. The erroneous patient synchronization request is not fulfilled by the deployment that received it. When a Wrong Home exception occurs, the requesting deployment's identification information is logged, together with a patient synchronization message.

Another exception type, Message Format Error, indicates that a patient synchronization message was not formatted correctly. XML may be used to represent the patient data, and XML formatting errors would generate this exception type. Errors in the data itself do not generate this exception type. This type of exception causes a message to be sent to the requesting deployment telling it to log a Remote Exception Notification exception so that staff there will know that it sent an invalid message. The faulty patient synchronization message is not fulfilled by the receiving deployment. When a Message Format Error exception occurs, the requesting deployment's identification information is logged, together with a patient synchronization message.

A Data Format Error exception type indicates that data in a patient synchronization message was formatted incorrectly. For example, Data Format Error exceptions result when date fields do not contain dates, numeric fields do not contain numbers, or when foreign keys do not match a primary key in a different database. Data Format Error exceptions are logged after the message is received and before the data in the message is filed. This type of exception causes a message to be sent to the requesting deployment telling it to log a Remote Exception Notification exception so that staff there will know that it caused a Wrong Home Exception at the current deployment. The faulty data is not filed into the database. When a Data Format Error exception occurs, the requesting deployment's identification information is logged, together with a patient synchronization message.

Unsubscribed Update is another exception type that is generated when an update is received by a deployment for a patient that is not homed at the deployment and for which patient the deployment is not currently subscribed. The Unsubscribed Update exception reflects the assumption that a deployment only receives updates for patients it is subscribed to or for patients homed at the deployment. When this type of exception occurs, the Update Record is not filed by the receiving deployment. In addition, a patient synchronization message is logged.

Another exception type, Conflict Detected, indicates that an update was received that conflicts with the update history of the filed update. The conflict resolution work queue will use these exceptions to build its report. When this type of exception occurs, the request is not serviced. In addition, the sending deployment's identification information, and a patient synchronization message are logged.

An Unauthorized Request exception type is generated when a remote deployment requests a patient record but does not have the authority to do so. For example, suppose a remote deployment is required to receive patient consent before obtaining their record from the patient's home deployment. The remote deployment sends a Get Record message, but it has not secured the patient's consent. The receiving deployment will detect this condition and log an Unauthorized Request exception. In addition, the receiving deployment will send a message to the requesting deployment telling it to log a Remote Exception Notification exception so that staff there will know that it sent an unauthorized request. When this type of exception is generated, the offending request is not serviced. In addition, information regarding the requesting deployment's identification and a patient synchronization message are logged.

Local Activity Mode is another exception type that indicates that the end user did not wait for the Send Record message to finish transmitting all data before editing the patient record. For example, a patient may arrive at an urgent care clinic that is not the patient's home. If the clinician delivering care has the authority to edit the patient record before the Send Record message is complete and chose to use it, then this exception will be logged. Get Record responses are allowed to continue despite the fact that a Local Activity Mode exception occurred. When this type of exception occurs, the patient will be synchronized with the patient's home deployment. In addition, the identity of the user who chose to go into Local Activity Mode, a reason for going into Local Activity Mode, and information about the patient requested and the patient's home deployment are logged.

Another exception type, Synchronous Request Failed, indicates that a synchronous request, such as Get Summary, Get Home, or Find Patient, timed out or returned unexpected results. When this type of exception occurs, a message is sent to the requesting deployment to log a Remote Exception Notification indicating that the requesting deployment did not respond as expected to the synchronous request. In addition, a message is sent to the requesting deployment, telling it to log a Remote Exception Notification exception so that staff there will know that it did not respond as expected to the synchronous request. The user is notified of the exception. When a Synchronous Request Failed occurs, the deployment identification information of the receiving deployment and the reason for failure, either the bad results or the fact that the request timed out, are logged.

Another exception type, Remote Exception Notification, indicates that an exception occurred on a remote deployment and the current deployment needs to be notified. Specific examples of Remote Exception Notification exceptions include Wrong Home and Message Format Exception. When a Remote Exception Notification occurs, the deployment identification information of the deployment generating the exception, the exception type generated, and the information corresponding to the exception are logged.

Another exception type, General Exception, indicates an error condition not indicated by the exception types described above. When a General Exception occurs, a description of the exception is logged.

Version Skew

Version skew refers to the ability of deployments that are not using the same version of software to exchange patient record data. When a new release of software is available, a customer goes through the process of evaluating and testing the new release, and they may have to train staff on new features. This process can take several months; for a community with several deployments it becomes even longer, as each deployment may have specific needs and requirements. Version skew is a technique to enable a community to move to a newer version of software in a staggered manner, one (or a few) deployments at a time. This should not impact the ability of the upgraded deployment to fully participate in the Community, or create any requirements for other community participants that are not upgrading at the same time. It is important to understand that having deployments on different versions introduces some overhead in the system 10. Therefore, version skew should not be viewed as a long term solution, but as a way of letting deployments communicate with each other until they are brought to the same version within a manageable timeframe.

There are two main scenarios to deal with concerning version skew: (1) when a remote deployment is on a higher version than the home deployment, and (2) when the home deployment is on the highest version among the deployments subscribed to a particular patient.

In both scenarios, when a deployment on a lower version receives a message from a deployment on a higher version, there might be data which is unknown to the lower version. The step-down cache is the mechanism used to store and display this information at the deployment on the lower version. It is also used to "echo back" (transmit back to the original sender) the information if needed.

Figure 20:
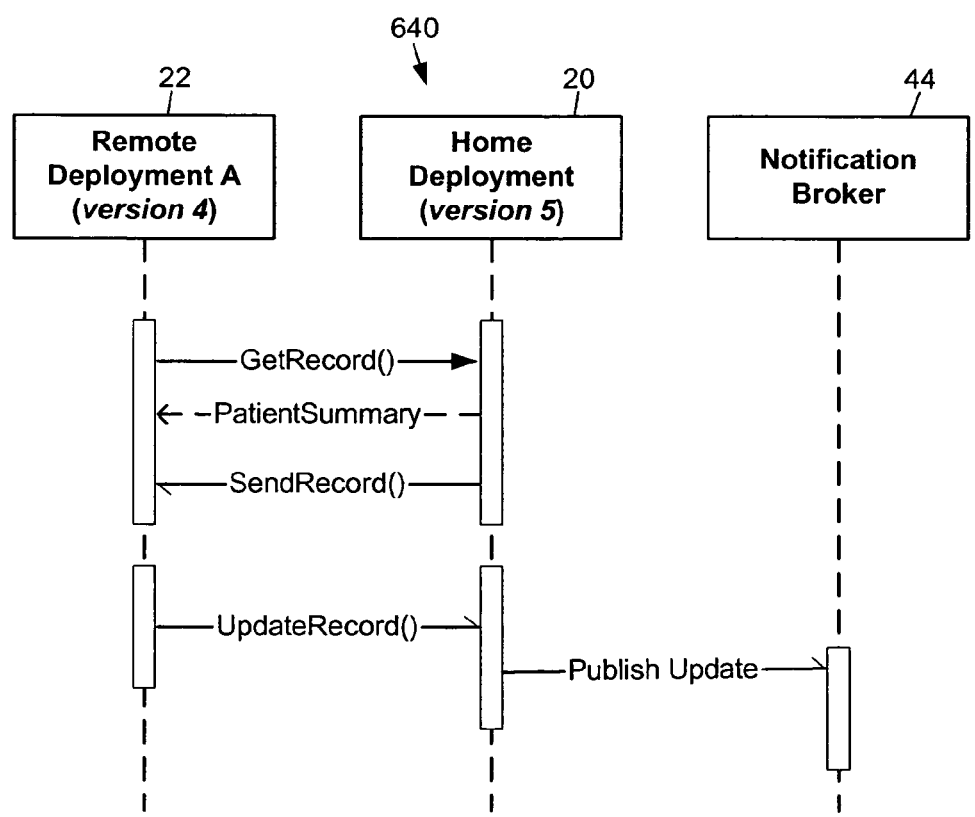
FIG. 20 is an exemplary block diagram illustrating a patient record pull when a home deployment is on a higher version.

FIG. 20 is a block diagram 640 illustrating an exemplary patient record synchronization when a home deployment is on a higher version. As shown in FIG. 23, patient P's home deployment 20 is on version 5. Patient P receives care at remote deployment A 22, which is on version 4.

The Get Record message received by the home deployment 20 includes an indication that the sender, deployment A 22, is on version 4. As a result, the Send Record message is downgraded for the remote deployment A's consumption. When an Update Record message is sent from the remote deployment 22 to the home deployment 20, the home deployment 20 upgrades any information that is in an older version format, files the update locally, and then publishes it, including "downgraded" information for all possible lower version subscribers.

Figure 21:
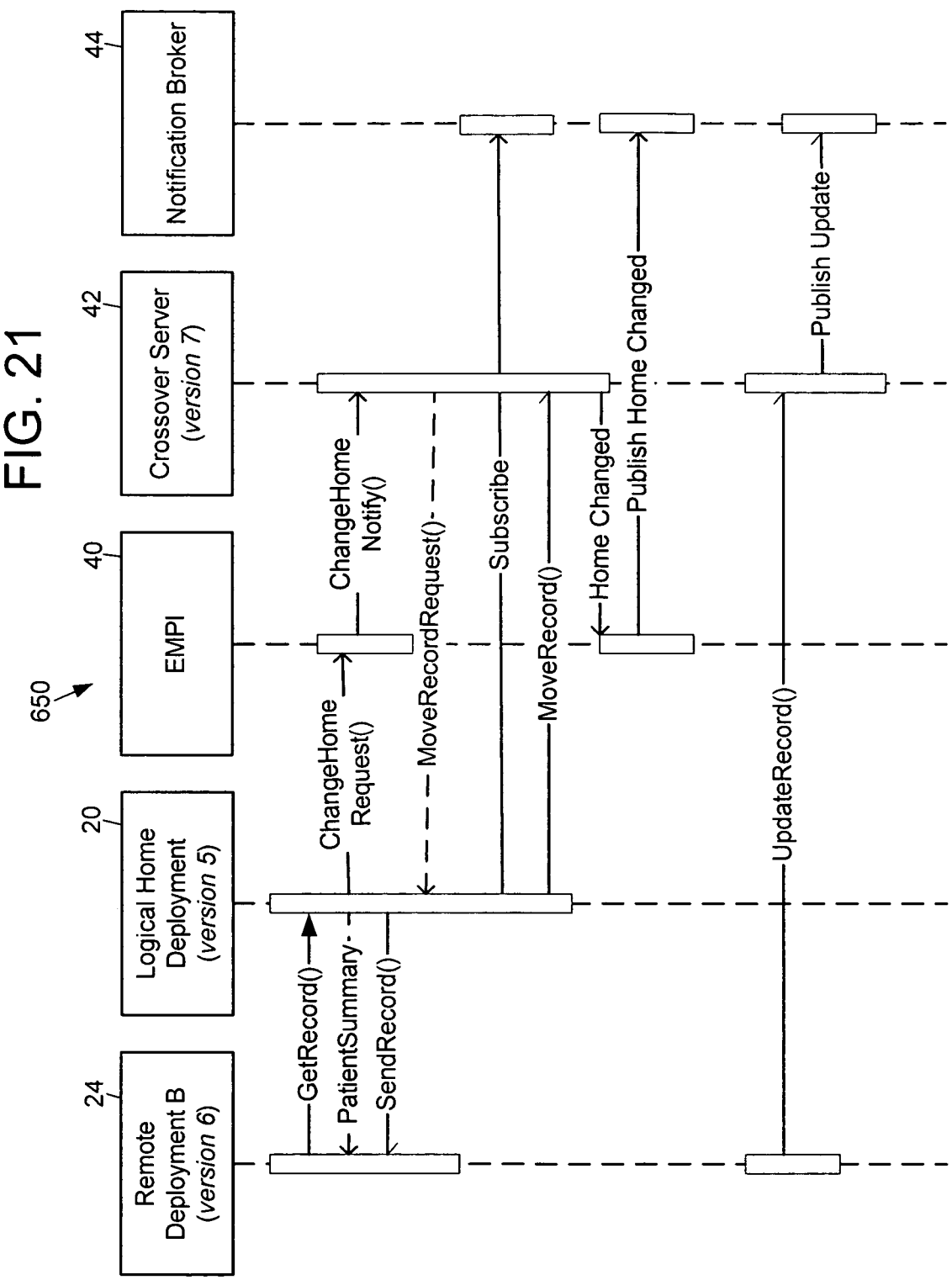
FIG. 21 is an exemplary block diagram illustrating a patient record pull when a home deployment is on a lower version.

FIG. 21 is a block diagram 650 illustrating an exemplary patient record synchronization when a home deployment is on a lower version. As shown in FIG. 21, patient T's home deployment 20 is on version 5. Patient T is seen on remote deployment B 24, which is on version 6.

In this scenario, the server where the patient's record is physically stored (which is called the "physical home"), and the deployment which represents that patient's location (called the "logical home") become distinct and separate, as the crossover server 42 becomes the physical home. Descriptions of logical and physical home are provided above.

As shown in FIG. 21, the patient's home deployment 20, logical home, detects that the Get Record request came from a deployment 24 on a higher version. The logical home enters a "switch home" mode, where the processing of any updates is suspended, while the processing of any Get Record requests continues. A Change Home request is sent to the EMPI 40. The EMPI 40 then sends a Change Home Notify message to the crossover server 42, to tell it that it is now the physical home of patient T.

The crossover server 42 sends a Move Record request back to the logical home 20 in order to get the record moved there. When the logical home 20 receives the request from the crossover server, it will then subscribe to the notification broker 44 to receive updates for the patient record. The logical home 20 then sends the Move Record message to the crossover server 42.

Once the whole record has moved to the crossover server 42, the crossover server 42 notifies the EMPI 40 with a Home Changed message. The EMPI 40 then publishes the new home location. When the logical home 20 receives the Home Changed message, it will send to the crossover server 42 any pending Update Record messages that it may have received while the home deployment was being changed. It should be noted that there is a small chance that a Get Record request may come to the logical home deployment 20 after it has received the message about the new home. In this case, handling it as a Wrong Home error type will prevent any data formatting issues.

The purpose of the crossover server 42 is to provide a physical home for a patient record that needs to be updated by a deployment using a version of software that exceeds the version in use at the record's home deployment 20. When a logical home is upgraded to a higher version of software, there is a process for transferring the patient records that can now be returned from the crossover server 42 to the logical home 20. Each patient record includes a record of the highest version of software that has edited it. As part of the upgrade, a post-release process marks all records which are both physically on the crossover server and updated by a deployment of a version lower or equal to the current version of logical home 20. This list of patient records is then automatically processed off-hours and a request to change the home deployment is initiated for each record. This will keep the number of patient records on the crossover server 42 limited over time.

Figure 22:
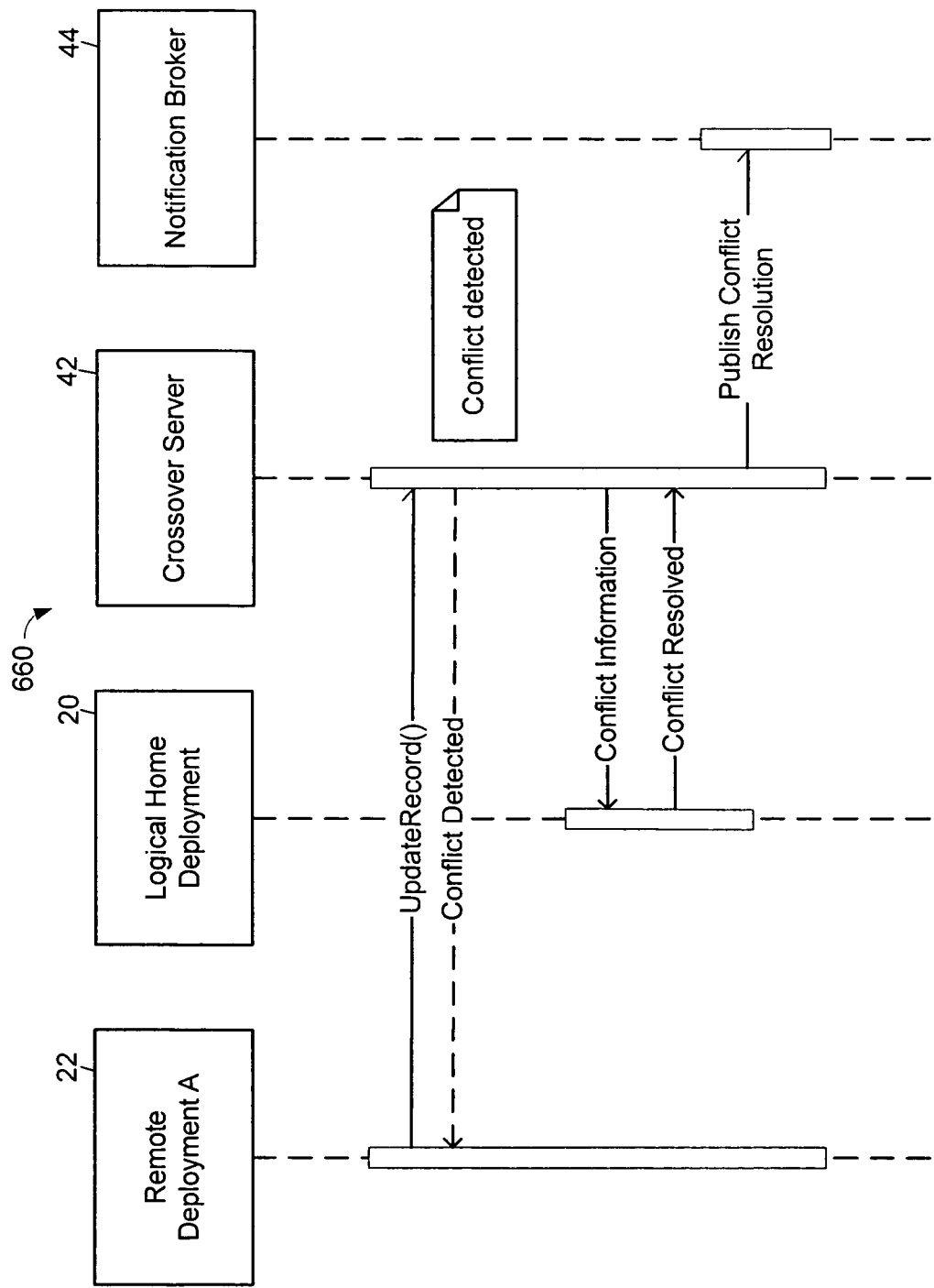
FIG. 22 is an exemplary block diagram illustrating conflict detection at a physical home and resolution at a logical home.

FIG. 22 is a block diagram 660 illustrating an exemplary conflict detection at a physical home and resolution at a logical home. All deployments in the system 10 check for conflicts, and the home deployments are responsible for resolving conflicts.

In the cases where the patient record's home deployment is on the highest software version among any remote subscribers, the conflicts are detected and resolved as described above with the extra step of bringing any remote deployment data up to the version of the home deployment. The extra step makes sure that the necessary comparisons are made on the data represented on the same version.

When a patient record is moved to the crossover server 42, the crossover server 42 becomes the physical home deployment for that record. Conflict is detected on the crossover server 42. Because the crossover server does not handle interactive users, conflicts are resolved on the logical home deployment. This can be achieved by introducing a special type of message, sent from the crossover server 42 to the logical home deployment 20, containing information about the conflict. This message is placed on a conflict resolution queue, and the tool designed to help users make the decisions about the proper content of the record operates on that message. Once the resolution is complete, a message containing the proper record contents is sent to the crossover server 42, which then publishes the conflict resolution message to all subscribed deployments.

It should be noted that required data elements are those that require a value in order for the system to work correctly. An example of such a data element is event type. Each patient contact should have this data element set to some value. When a required data element is added as part of the development process, there should be a way to specify a default value for the data element. This may be handled via a pre-release conversion. This method is applied to handle instances when an update from a lower version is received at the home deployment 20. That is, run the specified conversion on the current record to create a value for the data element, if there isn't one specified already.

A computed data element is one that is calculated (not directly edited) by either deriving a decision based on other values or by compiling data elements together (e.g. current meds list). For better efficiency, the sender sends the computed values. The receiver has the option to accept the computed values, or recalculate them. In the case of version skew, the receiver recalculates the computed data elements, which makes adding a new computed data element safe. However, changing the way a data element is computed between versions constitutes a change to the data element definition, which may not be allowed.

When there is a new data element in the newer version and there was a value in the row which was deleted, this value is removed when the update is stored. In order to achieve this, the following conditions should be present: (1) The deployment on the lower version stores the values of the new data elements, together with the appropriate row in the step down cache. (2) The deployment on the lower version recognizes when a row in the table is replaced vs. edited—in the first case, the value of the new data element corresponding to this row needs to be deleted, while in the second it needs to be preserved. (3) When the update is sent, the information about the table needs to contain the "native" data as well as the data from the newer version.

If the database schema changes, e.g. if a special case requires the removal of a data element, a data inversion is provided. This data inversion is able to change the data back to using the old data element as needed, such as when newer version information is sent to an older version. If such an inversion is not possible, then the data element is preserved for backwards compatibility.

When a new selection list value is added to a selection list in a range, it may be one of two kinds: a data value, or a workflow value. A data value is one that represents a concept, or a piece of information, which is presented to the user (e.g. religion). Workflow values (as the name suggests) are used to determine application behavior.

For data values, the new selection list is created on the deployment with the lower version of the software (so that it can be displayed to the user), and it will be inactivated (so that a user cannot select it). When the deployment upgrades to a higher version that contains that selection list value, it is made active.

Because of the nature of workflow values, when a new selection list value is added, it is mapped to a previously existing value. When the value for that data element is sent, both the current and the mapped selection list values are sent, so that the lower version of the software can function based on the backward-compatible value. This is very similar to the concept of "inversion" mentioned above, and is enforced as part of the development process.

A receiver that is on the lower version stores the newer version's value in the step-down cache, so that the correct value is sent back out with the update.

A simple data element is one that does not fall in any of the other categories presented here. When a deployment on a higher version sends such data, the receiver, which is on a lower version, stores the data in the step-down cache. If the deployment on the lower version sends back an update that includes the group to which the new data element belongs, there is no need to actually "echo back" the value of this data element, since the publisher of the update (the home deployment) will already have the data (the lower version couldn't have changed it).

Although the technique for providing healthcare organizations the ability to allow for the convenient and expedient transfer of patient information between separate healthcare systems described herein, is preferably implemented in software, it may be implemented in hardware, firmware, etc., and may be implemented by any other processor associated with a healthcare enterprise. Thus, the routine(s) described herein may be implemented in a standard multi-purpose CPU or on specifically designed hardware or firmware as desired. When implemented in software, the software routine(s) may be stored in any computer readable memory such as on a magnetic disk, a laser disk, or other machine accessible storage medium, in a RAM or ROM of a computer or processor, etc. Likewise, the software may be delivered to a user or process control system via any known or desired delivery method including, for example, on a computer readable disk or other transportable computer storage mechanism or over a communication channel such as a telephone line, the Internet, etc. (which are viewed as being the same as or interchangeable with providing such software via transportable storage medium).

While the present invention has been described with reference to specific examples, which are intended to be illustrative only and not to be limiting of the invention, it will be apparent to those of ordinary skill in the art that changes, additions or deletions may be made to the disclosed embodiments without departing from the spirit and scope of the invention.

The invention claimed is:

1. A healthcare information management system for synchronizing data in different instances of a first patient record that are maintained by different deployments and where the instances of the first patient record maintained by the different deployments may be updated simultaneously so that the first patient record maintained by different deployments may be different versions at any time, the system comprising:
   a plurality of deployments including at least a first deployment wherein each deployment includes at least one server including a processor that runs a computer program, and each of the plurality of deployments maintains a generation level for the instance of the first patient record stored by the deployment;
   a communication network communicatively coupling the first deployment server to other remote deployment servers;
   wherein the first deployment server performs a program to carry out the steps of:
      storing a first instance of the first patient record;
      receiving updates to the first patient record from at least one other remote deployment accessing and modifying the patient record, the update including the generation level corresponding to the patient record at the other remote deployment;
      determining when whether a received update builds on the first instance of the first patient record based on the generation level of the first instance and the generation level of the received update; and
      when the received update builds on the first instance, using the update received from the remote deployment to reconcile the modification with the first instance of the first patient record thereby generating a new version of the first instance and publishes the reconciled modifications to all deployments while the remote deployment server is accessing and modifying the patient record;
   when the received update does not build on the first instance, determining if the first instance was built on the incoming update and disregarding the update as a duplicate if the first instance builds on the incoming data; and
   if the received update does not build on the first instance and the first instance does not build on the received update, moving the update to a conflict queue.

2. The system of claim 1 wherein the first deployment is further arranged to, when a request is received for a copy of the first patient record, transmit the first instance of the first patient record to the requesting deployment, the plurality of deployments including at least a second deployment arranged to request a copy of the first patient record from the first deployment, to receive the first patient record from the first deployment, to store the received first patient record as a second instance of the first patient record, to receive updates to the second instance of the first patient record and to provide the updates to the second instance of the first patient record to the first deployment.

3. The system of claim 2 wherein the first deployment is further arranged to, when an update is used to modify the first instance of the first patient record, publish the modification as an update to other system deployments that store instances of the first patient record.

4. The system of claim 3 wherein, when a deployment receives a published update, the receiving deployment is arranged to determine when the published update builds on the instance of the first patient record stored by the deployment and, when the published update builds on the instance of the first patient record stored by the deployment, to use the published update to modify the instance of the first patient record stored by the deployment.

5. The system of claim 3 wherein the first deployment is arranged to publish updates to other deployments at least one of (1) whenever the first deployment makes updates to the first instance; (2) whenever the second deployment accesses the second instance of the first patient record and (3) periodically at specific trigger instances.

6. The system of claim 1 wherein a second deployment stores a second instance of the first patient record and transmits the update to the first patient record, the first deployment is arranged to determine that the received update builds on the first instance by determining that both the first deployment and the second deployment had the same version of the first patient record prior to the second deployment providing the update.

7. The system of claim 6 wherein the first deployment is arranged to determine that the received update builds on the first instance when the first deployment had an older version of the first patient record than the second deployment prior to the second deployment providing the update.

8. A healthcare information management system for synchronizing data in different instances of a first patient record that are maintained by different deployments and where the instances of the first patient record maintained by the different deployments may be updated simultaneously so that the first patient record maintained by different deployments may be different versions at any time, the system comprising:
- a plurality of deployments including at least a first deployment wherein each deployment includes at least one server including a processor that runs a computer program, and each of the plurality of deployments maintains a generation level for the instance of the first patient record stored by the deployment;
- a communication network communicatively coupling the first deployment server to the other deployment servers;
- wherein the first deployment server performs a program to carry out the steps of:
    - storing a first instance of the first patient record;
    - receiving updates to the first patient record from at least one other deployment accessing and modifying the patient record, the update including a generation level for the patient record at the deployment;
    - determining when a received update builds on the first instance of the first patient record; and
    - when the received update builds on the first instance, using the update to reconcile and modify the first instance of the first patient record thereby generating a new version of the first instance and publishes the reconciled modifications to all deployments while the other deployment server is accessing and modifying the patient record;
    - wherein the first deployment maintains a first update history for the first instance of the first patient record, the first update history identifying at least a first subset of the deployments that previously contributed to the first instance of the first patient record along with generation levels indicating at least a subset of the generations of the first instance of the first patient record to which the first subset of deployments contributed; and
- a second deployment maintains a second instance of the first patient record and a second update history for the second instance of the first patient record, the second update history identifying at least a second subset of the deployments that previously contributed to the second instance of the first patient record along with generation levels indicating at least a subset of the generations of the second instance of the first patient record to which the second subset of deployments contributed.

9. The system of claim 8 wherein a second deployment transmits the update and the second update history to the first deployment, the first deployment receives the update and the second update history from the second deployment and compares the first and second update histories to determine when the update received from the second deployment builds on the first instance of the first patient record.

10. The system of claim 8 wherein the first deployment is further arranged to, when a request is received for a copy of the first patient record, transmit the first instance of the first patient record to the requesting deployment, the plurality of deployments including at least a second deployment arranged to request a copy of the first patient record from the first deployment, to receive the first patient record from the first deployment, to store the received first patient record as a second instance of the first patient record, to receive updates to the second instance of the first patient record and to provide the updates to the second instance of the first patient record to the first deployment.

11. The system of claim 10 wherein the first deployment is further arranged to, when an update is used to modify the first instance of the first patient record, publish the modification as an update to other system deployments that store instances of the first patient record.

12. The system of claim 8 wherein, when (1) the received update does not build on the first instance, (2) the first instance does not build on the received update and (3) the first instance does not include the received update, the first deployment moves the update to a conflict queue.

13. A healthcare information management system for synchronizing data in different instances of a first patient record that are maintained by different deployments and where the instances of the first patient record maintained by the different deployments may be updated simultaneously so that the first patient record maintained by different deployments may be different versions at any time, the system comprising:
- a plurality of deployments including at least a first deployment wherein each deployment includes at least one server including a processor that runs a computer program, and each of the plurality of deployments maintains a generation level for the instance of the first patient record stored by the deployment;
- a communication network communicatively coupling the first deployment server to the other deployment servers;
- wherein the first deployment server performs a program to carry out the steps of:
- storing a first instance of the first patient record;
    - receiving updates to the first patient record from at least one other deployment accessing and modifying the patient record, the update including a generation level for the patient record at the deployment;
    - determining when a received update builds on the first instance of the first patient record; and
    - when the received update builds on the first instance, using the update to reconcile and modify the first instance of the first patient record thereby generating a new version of the first instance and publishes the reconciled modifications to all deployments while the other deployment server is accessing and modifying the patient record; and
- wherein:
    - the first instance of the first patient record includes data in a first set of data groups;
    - a second deployment stores a second instance of the first patient record where the second instance includes data in a second set of data groups;
    - the first deployment maintains a separate update history for each of the data groups in the first set of data groups;
    - the second deployment maintains a separate update history for each of the data groups in the second set of data groups;
    - each update history identifying at least a subset of the deployments that previously contributed to the data group along with generation levels indicating at least a subset of the generations of the data group to which the subset of deployments contributed; and
    - wherein the second deployment provides the update and associated update histories to the first deployment;
    - the first deployment is arranged to carry out the step of determining when a received update builds on the first instance of the first patient record by using the received update histories and the update histories associated with the data groups in the first instance of the first patient record to determine, on a data group by data group basis, when an update to a data group builds on the instance of the data group in the first instance of the first patient record; and
    - wherein, the step of using the update to modify the first instance of the first patient record includes using only updates that build on instances of data groups in the first instance of the first patient record to update the first instance.

14. The system of claim 13 wherein the first deployment is further arranged to, when a request is received for a copy of the first patient record, transmit the first instance of the first patient record to the requesting deployment, the plurality of deployments including at least a second deployment arranged to request a copy of the first patient record from the first deployment, to receive the first patient record from the first deployment, to store the received first patient record as a second instance of the first patient record, to receive updates to the second instance of the first patient record and to provide the updates to the second instance of the first patient record to the first deployment.

15. The system of claim 14 wherein the first deployment is further arranged to, when an update is used to modify the first instance of the first patient record, publish the modification as an update to other system deployments that store instances of the first patient record.

16. The system of claim 13 wherein, when (1) the received update does not build on the first instance, (2) the first instance does not build on the received update and (3) the first instance does not include the received update, the first deployment moves the update to a conflict queue.

* * * * *